| United States Patent [19] | [11] Patent Number: 4,618,571 |
| Ichijima et al. | [45] Date of Patent: Oct. 21, 1986 |

[54] SILVER HALIDE COLOR PHOTOGRAPHIC LIGHT-SENSITIVE MATERIAL

[75] Inventors: Seiji Ichijima; Hideo Usui; Naoyasu Deguchi, all of Kanagawa, Japan

[73] Assignee: Fuji Photo Film Co., Ltd., Kanagawa, Japan

[21] Appl. No.: 705,473

[22] Filed: Feb. 25, 1985

[30] Foreign Application Priority Data

Feb. 23, 1984 [JP] Japan .................................. 59-33059

[51] Int. Cl.$^4$ ...................... G03C 1/46; G03C 7/30; G03C 7/32; G03C 7/26
[52] U.S. Cl. .................................. 430/505; 430/543; 430/553; 430/555; 430/557; 430/558; 430/566; 430/955; 430/957; 430/958; 430/959
[58] Field of Search .............. 430/955, 957, 566, 553, 430/958, 555, 959, 557, 226, 505, 558

[56] References Cited

U.S. PATENT DOCUMENTS

| 4,108,663 | 8/1978 | Tanaka et al. | 430/957 |
| 4,248,962 | 2/1981 | Lau | 430/957 |
| 4,310,621 | 1/1982 | Odenwälder et al. | 430/957 |
| 4,390,618 | 1/1983 | Kobayashi et al. | 430/955 |
| 4,409,323 | 10/1983 | Sato et al. | 430/549 |
| 4,477,560 | 10/1984 | Koitabashi et al. | 430/553 |
| 4,511,649 | 4/1985 | Ogawa et al. | 430/557 |
| 4,524,130 | 6/1985 | Iwasa et al. | 430/557 |
| 4,528,263 | 7/1985 | Sugita et al. | 430/957 |

*Primary Examiner*—Mary F. Downey
*Attorney, Agent, or Firm*—Sughrue, Mion, Zinn, Macpeak & Seas

[57] ABSTRACT

A silver halide color photographic light-sensitive material comprising a support having thereon at least one silver halide emulsion layer, the color photographic light-sensitive material containing a coupler which releases a compound after the coupling reaction with the oxidation product of a developing agent, the released compound being capable of releasing further a photographically useful group by an oxidation-reduction reaction with the oxidation product of another developing agent. The compound used in the present invention is chemically stable and can release a photographically useful group under control; therefore the silver halide color photographic light-sensitive material containing the compound has good stability during storage and high sensitivity and provides a color image having good image qualities such as sharpness, graininess, color reproducibility, etc.

22 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a novel compound which is capable of releasing a photographically useful group at development.

BACKGROUND OF THE INVENTION

It is known that upon color development of silver halide color photographic materials, the oxidation products of aromatic primary amine color developing agents react with couplers to form indophenol, indoaniline, indamine, azomethine, phenoxazine, phenazine and similar dyes, thereby forming color images. In this system, color reproduction is usually accomplished by the subtractive color process; silver halide emulsions selectively sensitive to blue, green and red, and yellow, magenta and cyan color image-forming agents in a complementary relation therewith are used. For example, acylacetanilide or dibenzoylmethane type couplers are used to form yellow color images; pyrazolone, pyrazolobenzimidazole, cyanoacetophenone or indazolone type couplers are mainly used to form magenta color images; and phenol type couplers, such as phenols and naphthols, are mainly used to form cyan color images.

It is also known that couplers are used not only to form dye images as described above but also for the purpose of releasing photographically useful groups. For example, U.S. Pat. Nos. 3,227,554 and 3,148,062, and *Journal of the American Chemical Society*, Vol. 72, page 1533 (1950) disclose couplers which release a development inhibitor or a dye from the coupling position thereof on reacting with the oxidation products of color developing agents. Further, U.S. Pat. No. 3,705,801 discloses couplers which are capable of releasing a bleach inhibitor from the coupling position after the reaction of the couplers with the oxidation products of the developing agents. More recently, U.S. Pat. No. 4,390,618 discloses couplers which release a fogging agent from the coupling position after the reaction of the couplers with the oxidation products of the developing agents.

Moreover, compounds which do not form dyes but release a photographically useful group upon the reaction with the oxidation products of the developing agents have also been known. For example, U.S. Pat. No. 3,930,863 discloses hydroquinones which release a development inhibitor.

As is well known from the above-described patent specifications, compounds releasing a photographically useful group are used for purposes such as improvement in color reproducibility, improvement in graininess, improvement in sharpness, or increase of sensitivity.

It is common knowledge in the photographic art that a technique to control the rate of releasing a photographically useful group and the rate of diffusion into an emulsion is more important than a technique to control the photographic function of the photographically useful group in the compounds capable of releasing a photographically useful group. It is also disclosed that as the diffusibility of the development inhibitors released increases, the sharpness is more improved as described in European Patent Application EP 101621A. As an example of such techniques, couplers which release a photographically useful group having a timing group are disclosed in U.S. Pat. No. 4,248,962. These couplers have good properties to some extent since the increase in the rate of coupling with these couplers is recognized in comparison with couplers wherein the photographically useful group is directly connected to the coupling position. However, they are disadvantageous in that their function is decreased or likelihood of desensitization or formation of fog is increased by decomposition thereof during storage of films containing these couplers. This is because hydrolysis of bonds to which an electrophilic group is attached is unavoidable when the films are stored under high humidity. As a result the photographically useful group is released. Since the photographically useful group is structurally designed so as to diffuse due to its purpose, it can diffuse into other layers and contact with silver halide and affect the photographic properties. The fact that the photographic properties are affected is a fatal defect and thus elimination of such a defect has been desired.

SUMMARY OF THE INVENTION

Therefore, an object of the present invention is to provide a color photographic light-sensitive material which has good stability during storage and high sensitivity and provides a color image having good image qualities such as sharpness, graininess and color reproducibility, etc. by using a novel compound which is chemically stable and in which release of a photographically useful group can be controlled.

Other objects of the present invention will become apparent from the following detailed description and examples.

These objects of the present invention have been accomplished by a silver halide color photographic light-sensitive material comprising a support having thereon at least one silver halide emulsion layer, the color photographic layer-sensitive material containing a coupler which releases a compound after the coupling reaction with the oxidation product of a developing agent, the released compound being capable of releasing further a photographically useful group by an oxidation-reduction reaction with the oxidation product of another developing agent.

DETAILED DESCRIPTION OF THE INVENTION

The compounds according to the present invention can eliminate the above-described defects and further have excellent photographic properties.

Preferred couplers which can be used in the present invention are represented by the following general formula (I):

A—RED—PUG                    (I)

wherein A represents a coupler residue capable of releasing a RED—PUG group upon the coupling reaction with the oxidation product of a developing agent; RED represents a group capable of releasing a PUG group after the oxidation-reduction reaction with the oxidation product of another developing agent after the bonding to A is cleaved; and PUG represents a group which substantially exerts photographic function after the bonding to RED is cleaved.

In the general formula (I), preferred examples of the coupler residue represented by A are described below.

Suitable examples of the yellow color image forming coupler residue represented by A include those of pivaloyl acetanilide type, benzoyl acetanilide type, malonic diester type, malondiamide type, dibenzoylmethane type, benzothiazolyl acetamide type, malonic ester monoamide type, benzothiazolyl acetate type, benzoxazolyl acetamide type, benzoxazolyl acetate type, benzimidazolylacetamide type and benzimidazolyl acetate type, the coupler residues derived from hetero ring-substituted acetimides or hereto ring-substituted acetates involved in U.S. Pat. No. 3,841,880; the coupler residues derived from the acyl acetamides as described in U.S. Pat. No. 3,770,446, British Pat. No. 1,459,171, West German Patent Application (OLS) No. 2,503,099, Japanese Patent Application (OPI) No. 139738/75 and *Research Disclosure*, No. 15737; and the hetero ring type coupler residues as described in U.S. Pat. No. 4,046,574, etc.

Suitable examples of the magenta color image forming coupler residue represented by A include those of 5-oxo-2-pyrazoline type, pyrazolobenzimidazole type, pyrazoloimidazole type, pyrazolopyrazole type, pyrazolotetrazole type, pyrazolotriazole type, cyanoacetophenone type and N-hetero ring-substituted acylacetamide type coupler residues as described in West German Patent Application (OLS) No. 3,121,955, etc.

Suitable examples of the cyan color image forming coupler residue represented by A include those having a phenol nucleus or an a-naphthol nucleus.

Suitable examples of substantially non-color forming coupler residue represented by A include those of indanone type, acetophenone type, etc. and specific examples thereof are described in U.S. Pat. Nos. 4,052,213, 4,088,491, 3,632,345, 3,958,993, 3,961,959, 4,046,574 and 3,938,996, etc.

In the general formula (I), preferred examples of the group represented by RED include a hydroquinone, a catechol, a naphtholhydroquinone, an o-amino or p-amino phenol (the amino group may be substituted with a sulfonyl group or an alkyl group, etc.) and a bisphenol. The group derived from these compounds is connected to the coupler residue A through the oxygen atom which is formed by eliminating the hydrogen atom from the hydroxy group contained in its molecule or a linking group and has a group represented by PUG as a substituent.

In the general formula (I), the group represented by PUG include, in detail, a development inhibitor, a development accelerator, a fogging agent, a dye, a silver removing accelerator, a silver removing inhibitor, a silver halide solvent and a competing compound (a scavenger for the oxidation product of a developing agent), etc.

The compound represented by the general formula (I) releases a RED—PUG group upon the reaction with the oxidation product of a developing agent at the time of development. The RED—PUG can further undergo the oxidation-reduction reaction with the oxidation product of a developing agent to form OX—PUG wherein OX means an oxidized form of RED. The oxidation-reduction reaction is, for example, a reaction of converting an amino group to an imino group or a reaction of oxidizing a hydroxy group contained in RED to an oxo group. Then the OX—PUG reacts with a nucleophilic agent such as a hydroxy ion present at development to release PUG. For this purpose, for example, the Michael addition or elimination reaction to the double bond which forms a conjugated system with the carbonyl group contained in OX can be referred to.

The OX—PUG formed according to the above-described reaction process is less water-soluble than the RED—PUG. This is due to the difference in hydrophilic degree between the carbonyl group and the hydroxy group. From this fact it is understood that the rate of diffusion of the RED—PUG is greater than that of the OX—PUG in an emulsion. The rate of forming the OX—PUG from the RED—PUG naturally depends on the concentration of the oxidation product of a developing agent. When a large amount of the oxidation products of developing agents are generated, the RED—PUG which is formed upon the coupling reaction immediately forms the OX—PUG without time to diffuse and the OX—PUG successively releases the PUG. In contrast, when only a small amount of the oxidation products of developing agents are generated, the RED—PUG formed upon the coupling reaction has time to diffuse to some extent and forms the OX—PUG which successively releases the PUG.

As described above, with the compound according to the present invention, the range wherein the PUG diffuses can be controlled depending on the concentration of the oxidation product of a developing agent. This is believed to be one reason why the compound according to the present invention exhibits such excellent properties. For instance, when the PUG is a development inhibitor, a large improvement in graininess can be obtained and the sharpness is also improved. Further, when the PUG is a development accelerator, the degree of accelerating development is great and an increase in sensitivity is also observed.

It is apparent from the above explanation that the compound according to the present invention undergoes reaction by a completely different mechanism from heretofore known couplers having a timing group and thus the compound has different functions from the known couplers. Furthermore, it is clear that the compound according to the present invention is stable against oxidation by air and hydrolysis. This is because the compound has a structure wherein the RED is only oxidized after it is released from the A and the thus-formed oxidized OX then forms for the first time the electrophilic reaction site which undergoes an attack by a nucleophilic agent such as a hydroxy ion.

With respect to the compound according to the invention, the scope wherein A, RED and PUG can be selected is large and thus the compound can be employed in various photographic light-sensitive materials, for example, color nagative films, color reversal films, color positive films, etc. according to various known methods. In general, the compound can be used as a DIR coupler, a colored coupler, a competing coupler or a development accelerating coupler, etc. in combination with a main coupler, or it may be used as a main coupler in some cases. The layer to be incorporated can be selected from an appropriate layer such as a high-sensitive layer or a low-sensitive layer, etc. depending on its purpose.

The present invention includes a group of compounds which can be employed in various photographic light-sensitive material, for various purposes, and by various methods to be used as described above. This is because the compound according to the present invention possesses several features including that the properties of the product formed by the reaction with the oxidation product of a developing agent can be varied due to an appropriate selection of the coupling component A (for example, variation of dyes formed, variation of non-color forming products, etc.), that the control of rate of release of RED—PUG from A or the control of the range wherein RED—PUG functions can be easily achieved by an appropriate selection of RED, and that the kind of photographic function can be varied depending on the purpose by an appropriate selection of PUG.

In Japanese Patent Application (OPI) No. 138636/72, examples of couplers which release an ED compound (a reducing agent) are disclosed. However, the compounds are completely different from the compounds according to the present invention, since they are used only for the purpose of reducing the oxidation product of a developing agent. On the other hand, in the present invention it is significant to release PUG, and to control the release of PUG depending on the concentration of the oxidation product of a developing agent and simultaneously control the range of diffusion according to the excellent functions of the compounds.

An amount of the compound to be added according to the present invention can be varied depending on the structure of the compound to be used and the purpose for use, etc. but it is preferred to use the compound in a range of from $1\times10^{-6}$ to 1 mol, particularly from $1\times10^{-3}$ to $5\times10^{-1}$ mol per mol of silver.

The compound according to the present invention can be used individually or in combination with known couplers in a layer.

Of the compounds according to the present invention, couplers represented by the following general formula (IIa), (IIb) or (IIc) are particularly preferred.

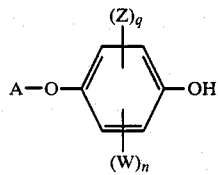  (IIa)

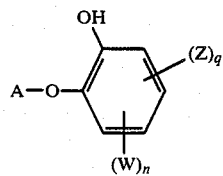  (IIb)

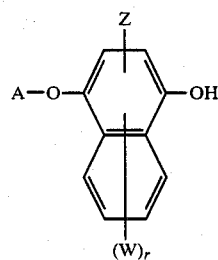  (IIc)

wherein Z represents a development inhibitor group; W represents a substituent selected from a halogen atom, an alkyl group, an alkoxy group, an alkylthio group, an arylthio group, an aryloxy group, a carbamoyl group, an N-alkyl (or dialkyl)carbamoyl group, an alkoxycarbonyl group, an aryloxycarbonyl group, an alkylsulfonyl group, an arylsulfonyl group, a sulfamoyl group, an N-alkyl (or dialkyl)sulfamoyl group, an N-arylcarbamoyl group, an N-arylsulfamoyl group, an alkanoyl group, arylcarbonyl group, a ureido group, an N-alkyl (or dialkyl)ureido group, an N-arylureido group, an alkylamino group, a benzamido group, an imido group, a nitro group, a cyano group, an alkylsulfonamido group, an arylsulfonamido group, a 5-membered or 6-membered heterocyclic group (containing as a hetero atom, a sulfur atom, a nitrogen atom or an oxygen atom), a hydroxy group, a carboxy group, an alkanoyloxy group, a urethane (including an N-alkyl urethane) group, a sulfo group, an amino group which may be substituted with an alkyl group or an aryl group, and an alkoxycarbonylamino group; q represents an integer from 1 to 2; n represents 0 or an interger from 1 to 3; q+n is not more than 4; r represents 0 or an integer from 1 to 5; A has the same meaning as defined in the general formula (I); and when two or more Z or W are present in the same coupler they each may be the same or different.

The alkyl moieties included in the above-described substituents represented by W may be any of substituted or unsubstituted, saturated or unsaturated, cyclic, straight chain or branched chain alkyl groups and contain from 1 to 22, preferably from 1 to 10 carbon atoms. Further the aryl moieties included in the above-described substituents represented by W may be further substituted and contain from 6 to 10 carbon atoms, and are preferably phenyl groups.

The couplers represented by the general formulae (IIa), (IIb) or (IIc) are generally a kind of DIR couplers. Although the DIR couplers have been heretofore used in color negative photographic light-sensitive materials, they do not exhibit sufficiently good properties in other color photographic light-sensitive materials. For example, when they are applied to color reversal photographic light-sensitive materials, the problem has been encountered that the development inhibiting function is not sufficiently generated since the color development processing for the color reversal photographic materials has generally a high developing activity.

The DIR couplers included in the present invention, however, show excellent properties with color reversal photographic light-sensitive materials as well. More specifically, the dual inhibiting functions, i.e., a function for inhibiting the color forming reaction due to consumption of the oxidation product of a developing agent by the group released from the coupler at the second development of the color reversal processing and a function for inhibiting development of silver by the development inhibitor consequently released can be exhibited.

It is believed that such effects naturally occur in color negative photographic light-sensitive materials and the excellent photographic properties which have not been achieved in the past can be obtained.

The effects of the present invention are particularly exhibited when A in the general formula (I) represents a coupler residue represented by the general formula (III), (IV), (V), (VI), (VII), (VIII), (IX), (X), (XI), (XII) or (XIII) described below. These couplers are preferred because of their high coupling rates.

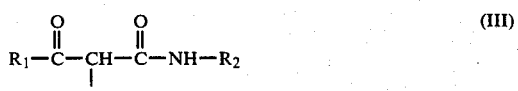  (III)

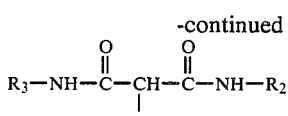

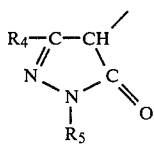

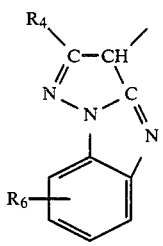

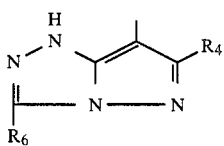

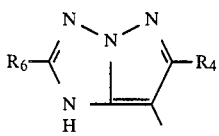

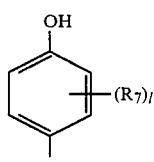

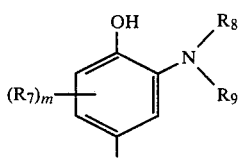

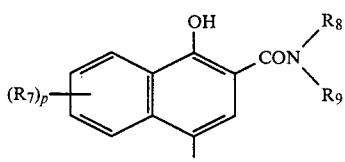

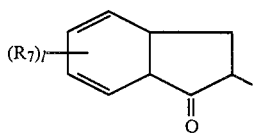

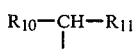

In the above-described formulae, a free bond attached to the coupling position indicates a position to which a group capable of being released upon coupling is bonded. When $R_1$, $R_2$, $R_3$, $R_4$, $R_5$, $R_6$, $R_7$, $R_8$, $R_9$, $R_{10}$ or $R_{11}$ in the above-described formulae contains a diffusion-resistant group, it is selected so that the total number of carbon atoms included therein is from 8 and 32 and preferably from 10 to 22. On the other hand, when it does not contain a diffusion-resistant group, the total number of carbon atoms included therein is preferably not more than 15.

In the following, $R_1$ to $R_{11}$, l, m and p in the above-described general formulae (III) to (XIII) are explained.

In the above-described formulae, $R_1$ represents an aliphatic group, an aromatic group, an alkoxy group or a heterocyclic group; and $R_2$ and $R_3$ each represents an aromatic group or a heterocyclic group.

The aliphatic groups represented by $R_1$ is preferably an aliphatic group containing from 1 to 22 carbon atoms, and may have substituents or not, and further, may have a chain form or a cyclic form. Preferable substituents therefor include an alkoxy group, an aryloxy group, an amino group, an acylamino group, a halogen atom, etc. which each may further have a substituent(s). Specific examples of aliphatic groups useful for $R_1$ include an isopropyl group, an isobutyl group, a tertbutyl group, an isoamyl group, a tert-amyl group, a 1,1-dimethylbutyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc.

In the case that $R_1$, $R_2$ or $R_3$ represent an aromatic group (especially a phenyl group), it may have a substituent. Such an aryl group as a phenyl group, etc. may be substituted with an alkyl group, an alkenyl group, an alkoxy group, an alkoxycarbonyl group, an alkoxycarbonylamino group, an aliphatic amido group, an alkysulfamoyl group, an alkylsulfonamido group, an alkylureido, alkyl-substituted succinimido group, etc. each containing 32 or less carbon atoms. The alkyl group therein may include an alkyl group which contains an aromatic group such as phenylene in its main chain. Further, a phenyl group represented by $R_1$, $R_2$ or $R_3$ may be substituted with an aryloxy group, an aryloxycarbonyl group, an arylcarbamoyl group, an arylamido group, an arylsulfamoyl group, an arylsulfonamido group, an arylureido group, etc., the aryl moiety of which groups each may be substituted with one or more alkyl groups wherein the number of carbon atoms is from 1 to 22 in total.

Furthermore, a phenyl group represented by $R_1$, $R_2$ or $R_3$ may be substituted with an amino group which includes an amino group substituted with a lower alkyl group having from 1 to 6 carbon atoms, a hydroxy group, a carboxy group, a sulfo group, a nitro group, a cyano group, a thiocyano group or a halogen atom.

In addition, $R_1$, $R_2$ or $R_3$ may represent a substituent formed by condensing a phenyl group and another ring, such as naphthyl group, a quniolyl group, an isoquinolyl group, a chromanyl group, a coumaranyl group, a tetrahydronaphthyl group, etc. These substituents may further have substituents in themselves.

In the case that $R_1$ represents an alkoxy group, the alkyl moiety thereof represents a straight chain or branched chain alkyl group having from 1 to 32 carbon atoms, preferably from 1 to 22 carbon atoms, an alkenyl group, a cyclic alkyl group or a cyclic alkenyl group, which each may be substituted with a halogen atom, an aryl group, an alkoxy group, etc.

In the case that $R_1$, $R_2$ or $R_3$ represents a heterocyclic group, the heterocyclic group is bonded to the carbon atom of the carbonyl group of the acyl moiety or the nitrogen atom of the amido moiety of an α-acylacetamido group through one of the carbon atoms forming the ring. Examples of such heterocyclic rings include thiophene, furan, pyran, pyrrole, pyrazole, pyridine, pyrazine, pyrimidine, pyridazine, indolizine, imidazole, thiazole, oxazole, triazine, thiadiazine, oxazine, etc. These rings may further have substituents on the individual rings.

$R_1$ is preferably a tert-butyl group or a substituted or unsubstituted phenyl group. $R_2$ and $R_3$ each is preferably a substituted or unsubstituted phenyl group.

In the above-described formula, $R_5$ represents a straight chain or branched chain alkyl group having from 1 to 32 carbon atoms, preferably from 1 to 22 carbon atoms (e.g., a methyl group, an isopropyl group, a tert-butyl group, a hexyl group, a dodecyl group, etc.), an alkenyl group (e.g., an allyl group, etc.), a cyclic alkyl group (e.g., a cyclopentyl group, a cyclohexyl group, a norbornyl group, etc.), an arlakyl group (e.g., a benzyl group, a β-phenylethyl group, etc.), a cyclic alkenyl group (e.g., a cyclopentenyl group, a cyclohexenyl group, etc.), etc., which groups each may be substituted with a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, a mercapto group, etc.

$R_5$ may further represent an aryl group (e.g., a phenyl group, an α- or β-naphthyl group, etc.). The aryl group may have one or more substituents. Specific examples of the substituents include an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an arkylthio group, an alkylamino group, a dialkylamino group, an anilino group, an N-alkylanilino group, an N-arylanilino group, an N-acylanilino group, a hydroxy group, a mercapto group, etc. A more preferable group for $R_5$ is a phenyl group which is substituted with an alkyl group, an alkoxy group, a halogen atom, etc. at least at one of the o-positions, because it is effective to restrain coloration of couplers remaining in film layers due to light or heat.

Furthermore, $R_5$ may represent a heterocyclic group (e.g., a 5-membered or 6-membered heterocyclic ring containing as a hetero atom a nitrogen atom, an oxygen atom or a sulfur atom, or a condensed ring thereof, with specific examples including a pyridyl group, a quinolyl group, a furyl group, a benzothiazolyl group, an oxazolyl group, an imidazolyl group, a naphthoxazolyl group, etc.), a heterocyclic group substituted with one or more substituents as defined for the above-described aryl group, an aliphatic acyl group, an aromatic acyl group, an alkylsulfonyl group, an arylsulfonyl group, an alkylcarbamoyl group, an arylcarbamoyl group, an alkylthiocarbamoyl group or an arylthiocarbamoyl group.

In the above-described general formulae, $R_4$ represents a hydrogen atom, a straight chain or branched chain alkyl group having from 1 to 32 carbon atoms, preferably from 1 to 22 carbon atoms, an alkenyl group, a cyclic alkyl group, an aralkyl group or a cyclic alkenyl group (which each may have one or more substituents as defined for the above-described substituent $R_5$), an aryl group or a heterocyclic group (which each also may have one or more substituents as defined for the above-described substituent $R_5$), an alkoxycarbonyl group (e.g., a methoxycarbonyl group, an ethoxycarbonyl group, a stearyloxycarbonyl group, etc.), an aryloxycarbonyl group (e.g., a phenoxycarbonyl group, a naphthoxycarbonyl group, etc.), an aralkyloxycarbonyl group (e.g., a benzyloxycarbonyl group, etc.), an alkoxy group (e.g., a methoxy group, an ethoxy group, a heptadecyloxy group, etc.), an aryloxy group (e.g., a phenoxy group, a tolyloxy group, etc.), an alkylthio group (e.g., an ethylthio group, a dodecylthio group, etc.), an arylthio group (e.g., a phenylthio group, an α-naphthylthio group, etc.), a carboxy group, an acylamino group (e.g., an acetylamino group, a 3-[(2,4-di-tert-amylphenoxy)acetamido]benzamido group, etc.), a diacylamino group, an N-alkylacylamino group (e.g., an N-methylpropionamido group, etc.), an N-arylacylamino group (e.g., an N-phenylacetamido group, etc.), a ureido group (e.g., a ureido group, an N-arylureido group, an N-alkylureido group, etc.), a urethane group, a thiourethane group, an arylamino group (e.g., a phenylamino group, an N-methylanilino group, a diphenylamino group, an N-acetylanilino group, a 2-chloro-5-tetradecanamidoanilino group, etc.), an alkylamino group (e.g., a n-butylamino group, a methylamino group, a cyclohexylamino group, etc.), a cycloamino group (e.g., a piperidino group, a pyrrolidino group, etc.), a heterocyclic amino group (e.g., a 4-pyridylamino group, a 2-benzoxazolylamino group, etc.), an alkylcarbonyl group (e.g., a methylcarbonyl group, etc.), an arylcarbonyl group (e.g., a phenylcarbonyl group, etc.), a sulfonamido group (e.g., an alkylsulfonamido group, an arylsulfonamido group, etc.), a carbamoyl group (e.g., an ethylcarbamoyl group, a dimethylcarbamoyl group, an N-methylphenylcarbamoyl group, an N-phenylcarbamoyl, etc.), a sulfamoyl group (e.g., an N-alkylsulfamoyl group, an N,N-dialkylsulfamoyl group, an N-arylsulfamoyl group, an N-alkyl-N-arylsulfamoyl group, an N,N-diarylsulfamoyl group, etc.), a cyano group, a hydroxy group, a mercapto group, a halogen atom or a sulfo group.

$R_4$ in the general formula (V) is preferably an acylamino group, a ureido group or an arylamino group. $R_4$ in the formulae (VI), (VII) and (VIII) is preferably a straight chain or branched chain alkyl group, an alkenyl group, a cyclic alkyl group, an aralkyl group or a cyclic alkenyl group.

In the above-described formuale, $R_6$ represents a hydrogen atom, or a straight chain or branched chain alkyl group having from 1 to 32 carbon atoms, preferably from 1 to 22 carbon atoms, an alkenyl group, a cyclic alkyl group, an aralkyl group or a cyclic alkenyl group, which each may have one or more substituents as defined for the above-described substituent $R_5$.

Further, $R_6$ may represent an aryl group or a heterocyclic group, which each may have one or more substituents as defined for the above-described substituent $R_5$.

Furthermore, $R_6$ may represent a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

$R_6$ in the general formula (VI) is preferably a hydrogen atom. $R_6$ in the general formulae (VII) and (VIII) is preferably a straight chain or branched chain alkyl group, an alkenyl group, a cyclic alkyl group, an aralkyl group or a cyclic alkenyl group.

In the above-described formulae, $R_7$, $R_8$ and $R_9$ each represents a group which has been employed in conventional 4-equivalent type phenol or α-naphthol couplers. Specifically, $R_7$ represents a hydrogen atom, a halogen atom, an alkoxycarbonylamino group, an aliphatic hydrocarbon residue, an N-arylureido group, an acylamino group, an —O—$R_{12}$ group or an —S—$R_{12}$ group (wherein $R_{12}$ is an aliphatic hydrocarbon residue). When two or more of $R_7$'s are present in one molecule, they may be different from each other. The above-described aliphatic hydrocarbon residues include those having substituents. In the case that these substituents include an aryl group, the aryl group may have one or more substituents as defined for the above-described substituent $R_5$.

$R_7$ in the general formula (IX) is preferably an acylamino group or a ureido group at the 2-position; an acylamino group or an alkyl group at the 5-position; or a hydrogen atom or a chlorine atom at the 6-position. $R_7$ in the general formula (XI) is preferably a hydrogen atom, an acylamino group, a sulfonamido group or an alkoxycarbonylamino group.

$R_8$ and $R_9$ each represents an aliphatic hydrocarbon residue, an aryl group or a heterocyclic group. Either of them may be a hydrogen atom. The above-described groups for $R_8$ and $R_9$ may further have certain substituents. Furthermore, $R_8$ and $R_9$ may combine with each other and form a nitrogen-containing heterocyclic nucleus. More specifically, the above-described aliphatic hydrocaron residues includes both saturated and unsaturated residues, wherein each may have a straight chain form, a branched chain form or a cyclic form. Preferred examples thereof include an alkyl group (e.g., a methyl group, an ethyl group, a propyl group, an isopropyl group, a butyl group, a tertbutyl group, an isobutyl group, a dodecyl group, an octadecyl group, a cyclobutyl group, a cyclohexyl group, etc.) and an alkenyl group (e.g., an allyl group, an octenyl group, etc.). The above-described aryl group includes a phenyl group, a naphthyl group, etc. Representatives of the above-described heterocyclic groups include a pyridinyl group, a quinolyl group, a thienyl group, a piperidyl group, an imidazolyl group, etc. These aliphatic hydrocarbon residues, aryl groups and heterocyclic groups each may be substituted with a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, a morpholino group, etc.

$R_8$ in the general formula (XI) is preferably a hydrogen atom. $R_9$ in the general formula (XI) is preferably a phenyl group, an alkyl group, an alkenyl group, a cyclic alkyl group, an aralkyl group or a cyclic alkenyl group.

In the above-described formulae, l represents an integer of 1 to 4, m represents an integer of 1 to 3, and p represents an integer of 1 to 5.

In the above-described formula, $R_{10}$ represents an arylcarbonyl group, an alkanoyl group having from 2 to 32 carbon atoms, preferably from 2 to 22 carbon atoms, an arylcarbamoyl group, an alkanecarbamoyl group having from 2 to 32 carbon atoms, preferably from 2 to 22 carbon atoms, an alkoxycarbonyl group having from 2 to 32 carbon atoms, preferably from 2 to 22 carbon atoms or an aryloxycarbonyl group, which each may be substituted. Examples of the substituents include an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group, an aryl group, etc.

In the above-described formula, $R_{11}$ represents an arylcarbonyl group, an alkanoyl group having from 2 to 32 carbon atoms, preferably from 2 to 22 carbon atoms, an arylcarbamoyl group, an alkanecarbamoyl group having from 2 to 32 carbon atoms, preferably from 2 to 22 carbon atoms, an alkoxycarbonyl group having from 2 to 32 carbon atoms, preferably from 2 to 22 carbon atoms, an aryloxycarbonyl group, an alkanesulfonyl group having from 1 to 32 carbon atoms, preferably from 1 to 22 carbon atoms, an arylsulfonyl group, an aryl group or a 5-membered or 6-membered heterocyclic group (containing as a hetero atom a nitrogen atom, an oxygen atom or a sulfur atom, with specific examples including a triazolyl group, an imidazolyl group, a phthalimido group, a succinimido group, a furyl group, a pyridyl group, a benzotriazolyl group, etc.), which each may have one or more substituents as defined for the above-described substituent $R_{10}$.

Preferred development inhibitor groups represented by Z in the general formulae (IIa), (IIb) or (IIc) can be represented by the following general formulae (XIV) to (XXII). In these general formulae, a free bond indicates a position at which the development inhibitor group is bonded to the RED portion.

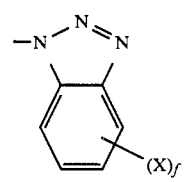

(XIV)

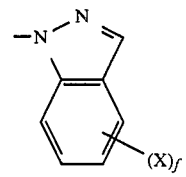

(XV)

-continued

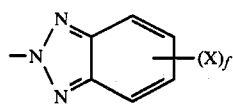 (XVI)

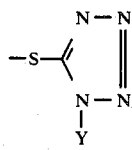 (XVII)

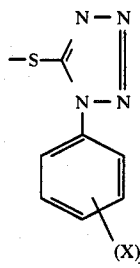 (XVIII)

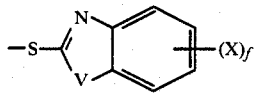 (XIX)

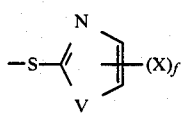 (XX)

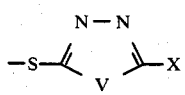 (XXI)

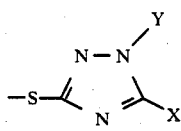 (XXII)

In the above-described formulae, X represents a substituent. Preferred examples of the substituent include a hydrogen atom, a halogen atom, an alkyl group, an alkanamido group, an alkoxy group, a sulfonamido group, an aryl group, an alkylthio group, an N-(mono- or di-alkyl)amino group, an arylthio group, an alkoxycarbonyl group, an acyloxy group, a carbamoyl group, an N-(mono- or di-alkyl)carbamoyl group, a nitro group, a cyano group, an alkanesulfonyl group, an aryloxy group, an amino group, a ureido group, a sulfamoyl group, a hydroxy group, an anilino group, a heterocyclic group, a sulfenamido group and a carboxy group, etc.

In the above-described formulae, Y represents a substituent. Preferred examples of the substituent include a hydrogen atom, an alkyl group, a phenyl group and a heterocyclic group.

In the above-described formulae, V represents —O—, —S— or

wherein Y has the same meaning as defined above.

In the above-described formulae, f represents an integer of 1 to 2. When f represents 2, X's may be the same or different.

The alkyl moieties included in the substituents represented by X and Y may be any of straigh chain, branched chain or cyclic, saturated or unsaturated, substituted or unsubstituted alkyl groups and contain from 1 to 16, preferably from 1 to 10 carbon atoms. The aryl moieties included in the substituents represented by X and Y are preferably phenyl groups which may be substituted. Examples of the substituents are those as defined for X.

Specific examples of the compounds which can be used in the present invention are set forth below, but the present invention should not be construed as being limited thereto.

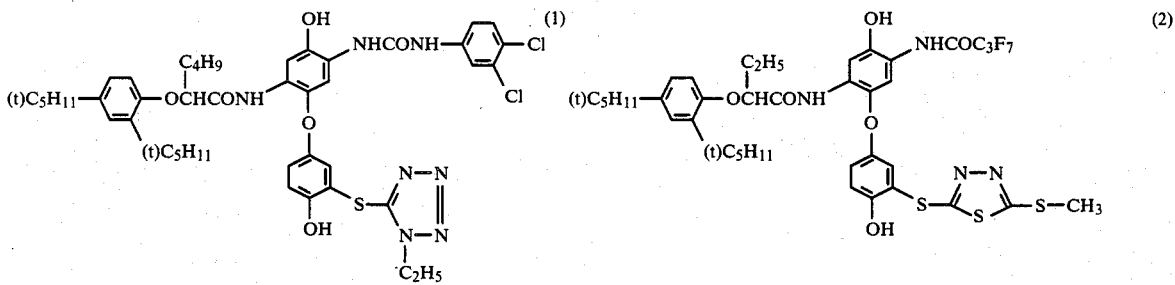

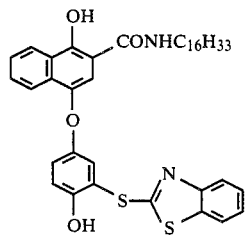
(3)
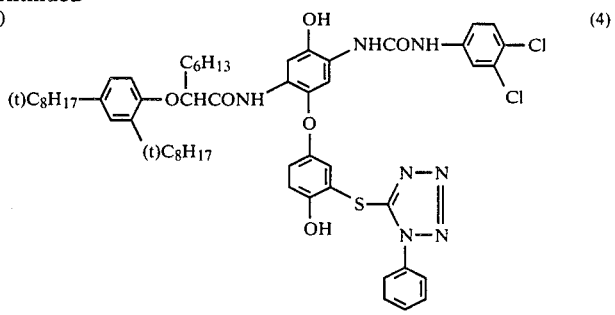
(4)
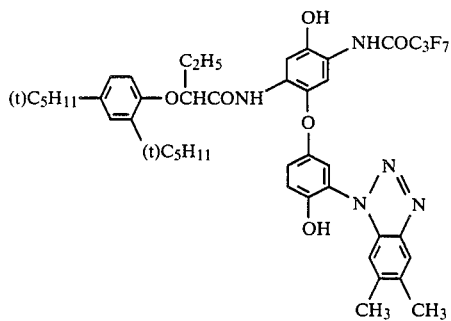
(5)
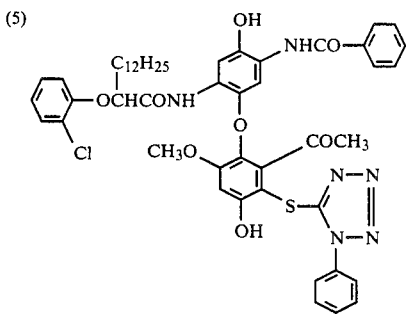
(6)
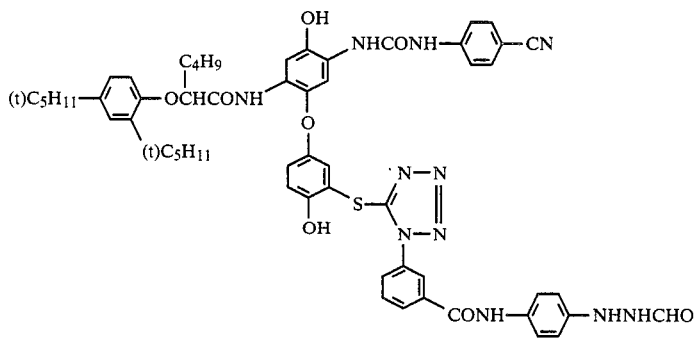
(7)
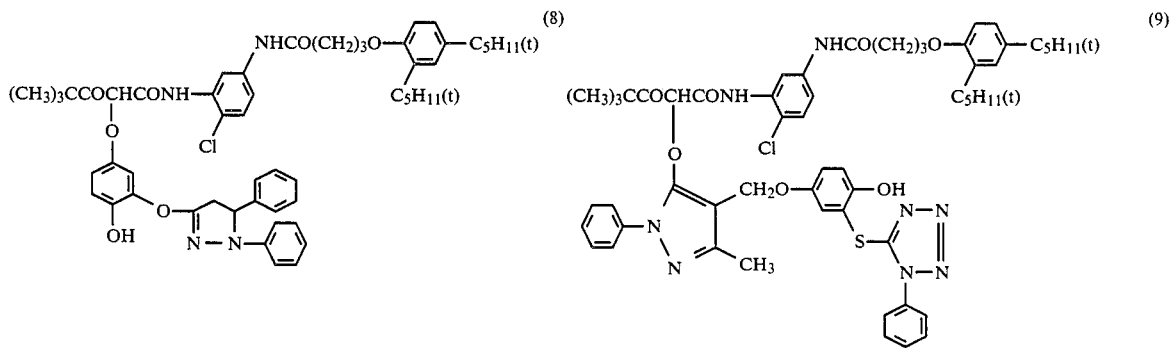
(8) (9)
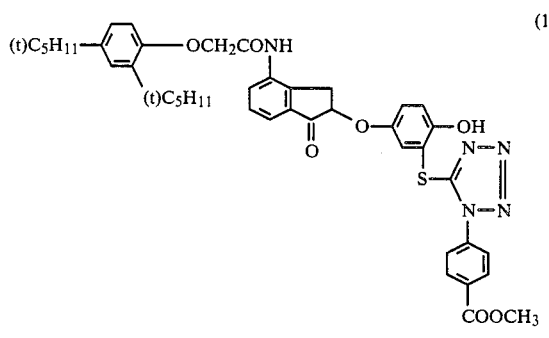
(10)
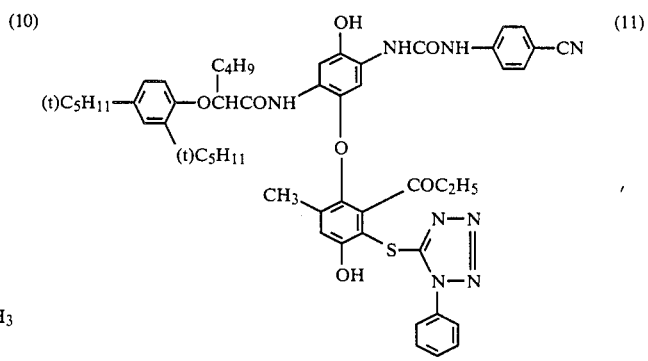
(11)

-continued
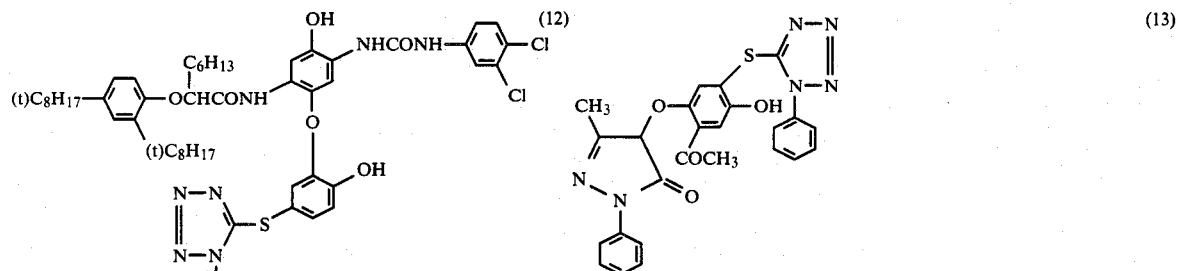
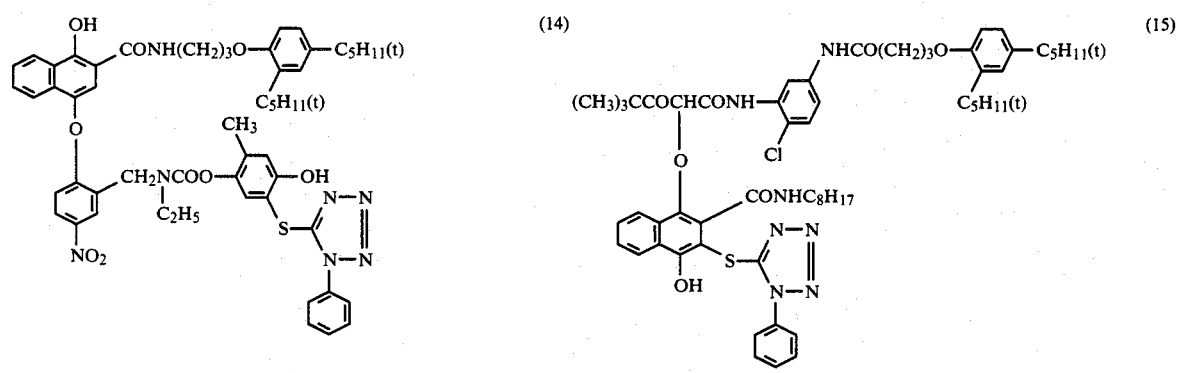
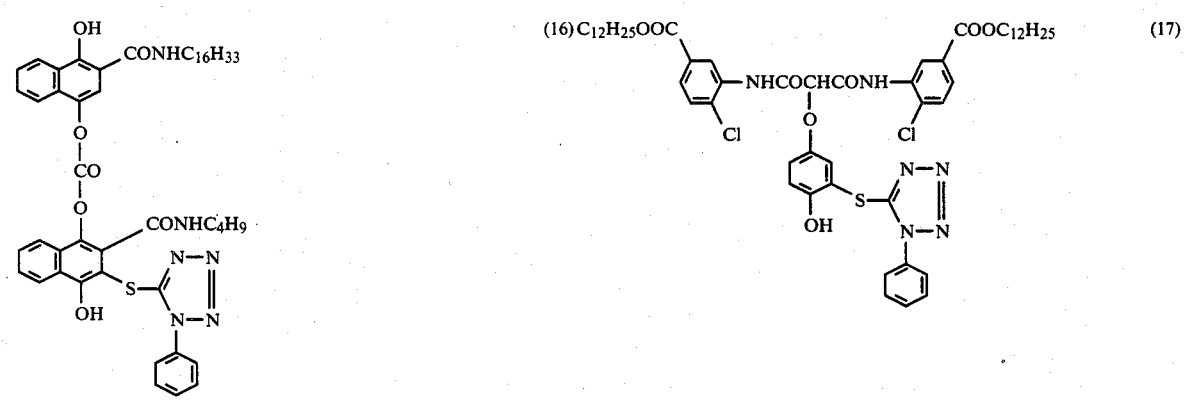
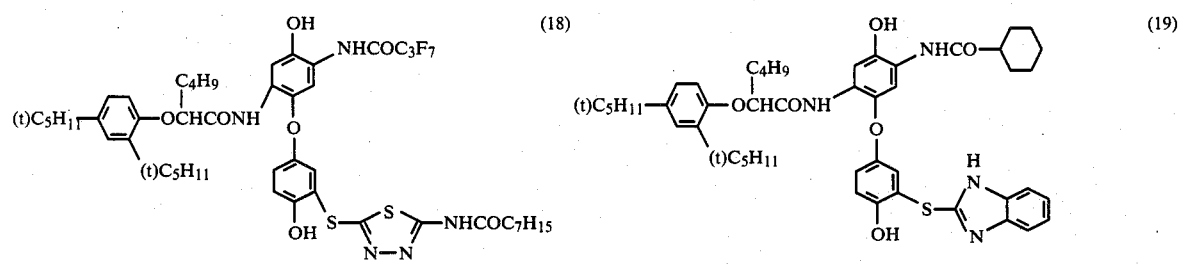

-continued
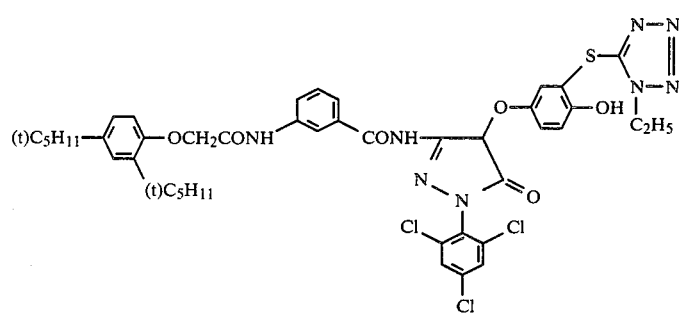 (20)
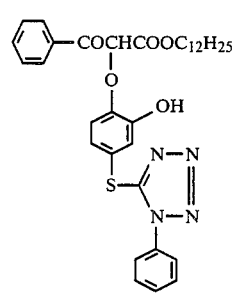 (21)
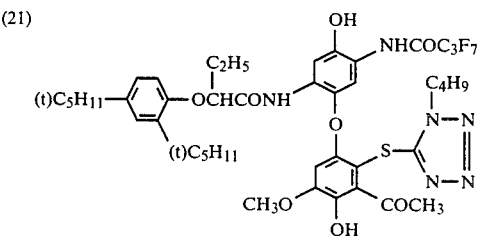 (22)
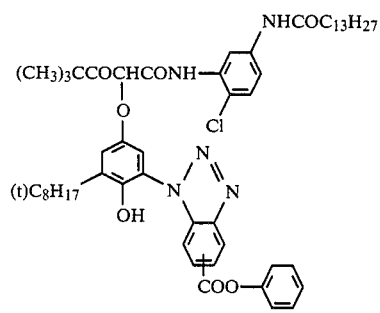 (23)
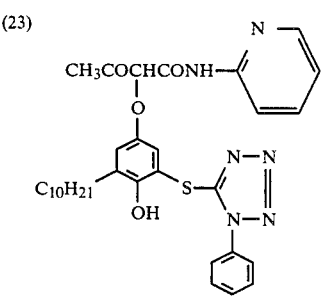 (24)
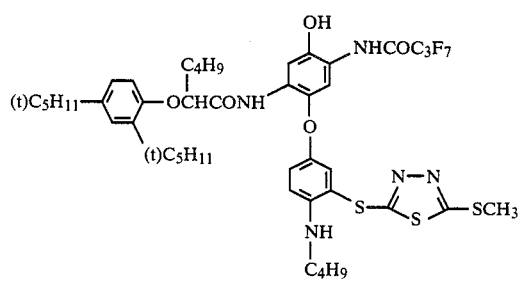 (25)
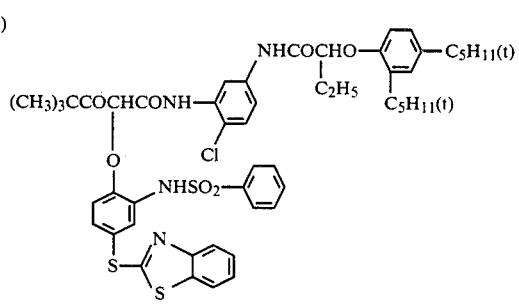 (26)
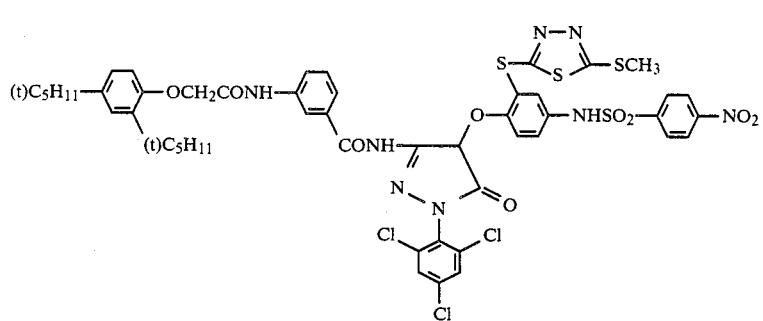 (27)

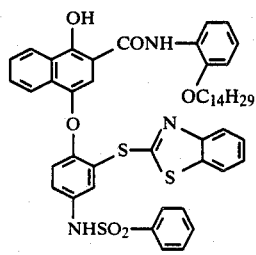
(28)
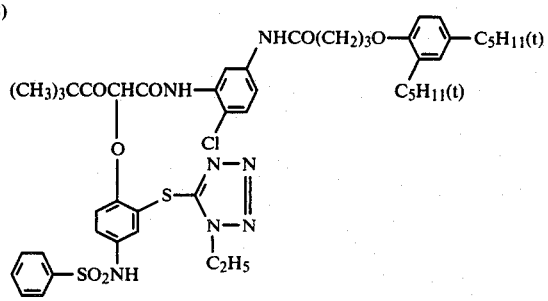
(29)
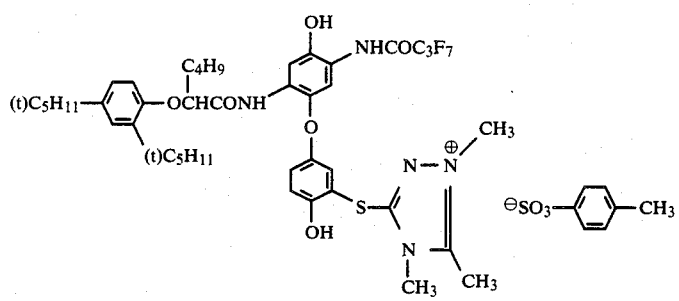
(30)
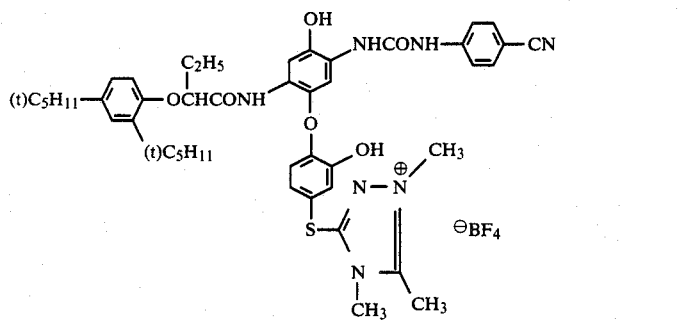
(31)
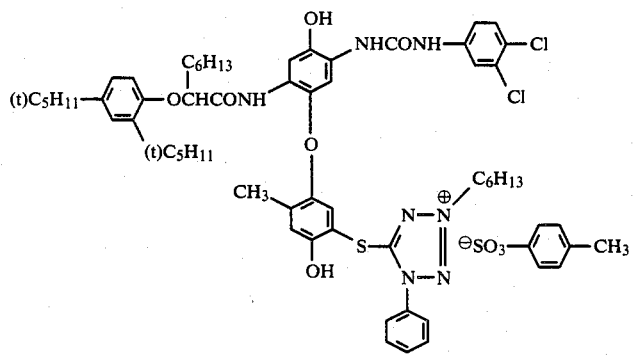
(32)
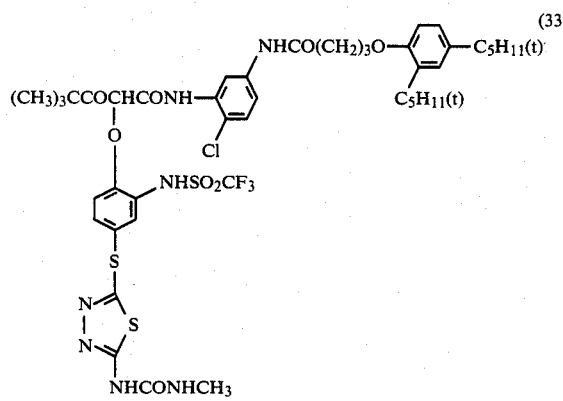
(33)
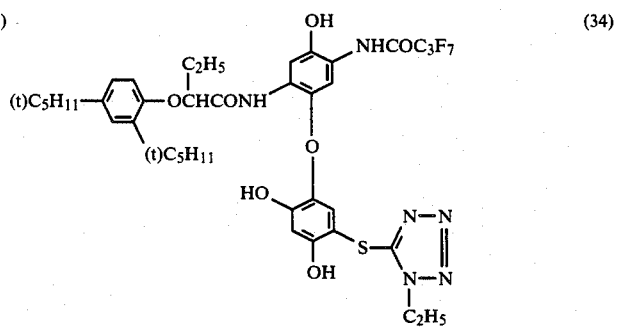
(34)

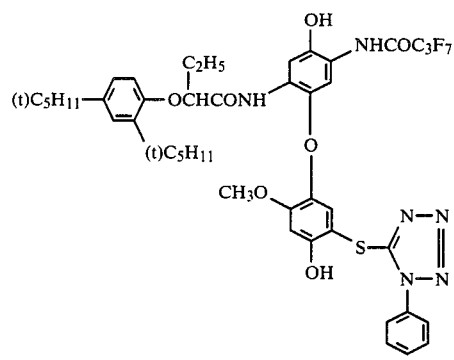 (35)

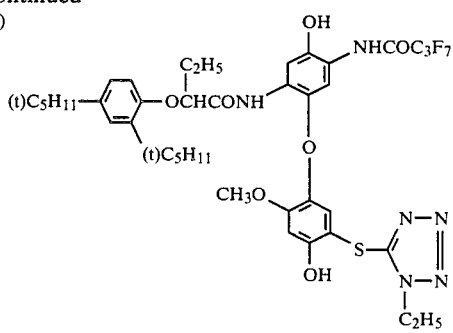 (36)

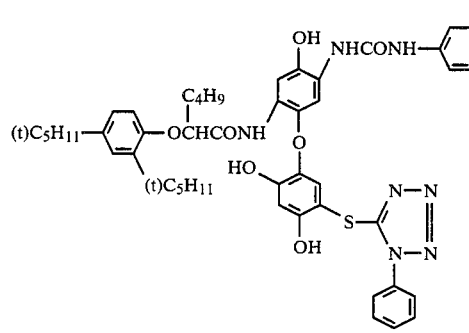 (37)

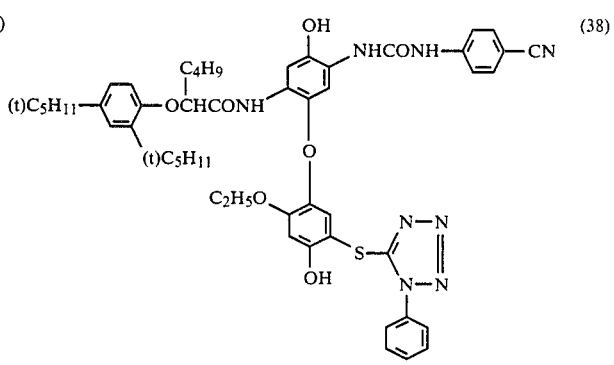 (38)

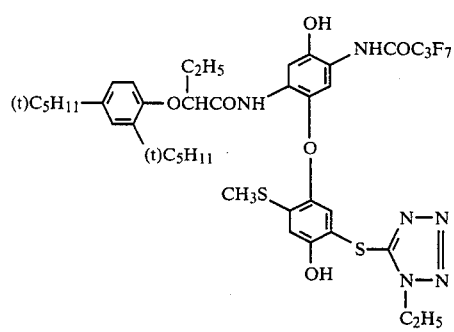 (39)

The couplers according to the present invention can be generally synthesized by employing known methods. Fundamentally, they can be prepared according to a synthesis route wherein each part is successively connected as illustrated in the following reaction scheme:

A→A—RED→A—RED—PUG wherein A, RED and PUG each has the same meaning as defined in the general formula (I), but in the reaction scheme the conversions of functional groups are included by which each step proceeds.

Typical examples of syntheses of the compounds according to the present invention are specifically shown below.

SYNTHESIS EXAMPLE 1

Synthesis of Compound (1)

Compound (1) was synthesized according to the following synthesis route:

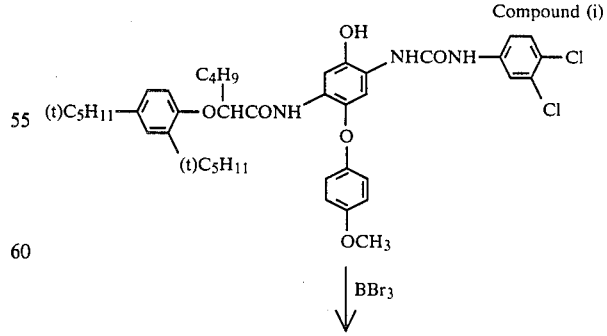

-continued

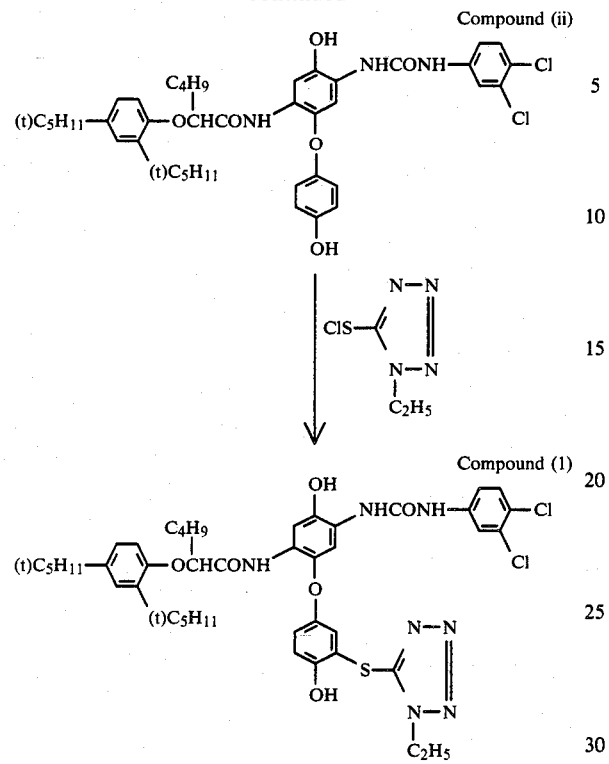

Step (1): Synthesis of Compound (ii)

To 200 ml of a dichloromethane solution containing 11.5 g of Compound (i) was added dropwise 3 ml of tribromoboran at 5° C. The mixture was stirred at the same temperature for 1.5 hours and raised to room temperature to which was added dropwise 50 ml of an aqueous solution containing 3 g of sodium hydrogen carbonate dissolved. After stirring for 10 minutes, the reaction mixture was placed in a separatory funnel and separated. The oil layer separated was washed with diluted hydrochloric acid and then washed with water until the washed water became neutral. After drying the oil layer with anhydrous sodium sulfate, the solvent was distilled off and the residue thus-obtained was recrystallized from a solvent mixture of ethyl acetate and n-hexane to obtain 8.5 g of Compound (ii).

Step (2): Synthesis of Compound (1)

To a solution containing 1.3 g of 1-ethyl-5-mercaptotetrazole dissolved in 10 ml of dichloromethane was added 0.8 ml of sulfuryl chloride at room temperature. After stirring for 1 hour, the solution was subjected to degassing by bubbling nitrogen gas for 30 minutes and added to 100 ml of a dichloromethane solution containing 7.5 g of Compound (ii) obtained in Step (1) above. After stirring for 5 hours at room temperature, the reaction mixture was placed in a separatory funnel and washed with water. The oil layer was dried with anhydrous sodium sulfate, the solvent was distilled off and the residue thus-obtained was recrystallized from a solvent mixture of ethyl acetate and n-hexane to obtain 7.2 g of the desired Compound (1).

SYNTHESIS EXAMPLE 2

Synthesis of Compound (29)

Compound (29) was synthesized according to the following synthesis route:

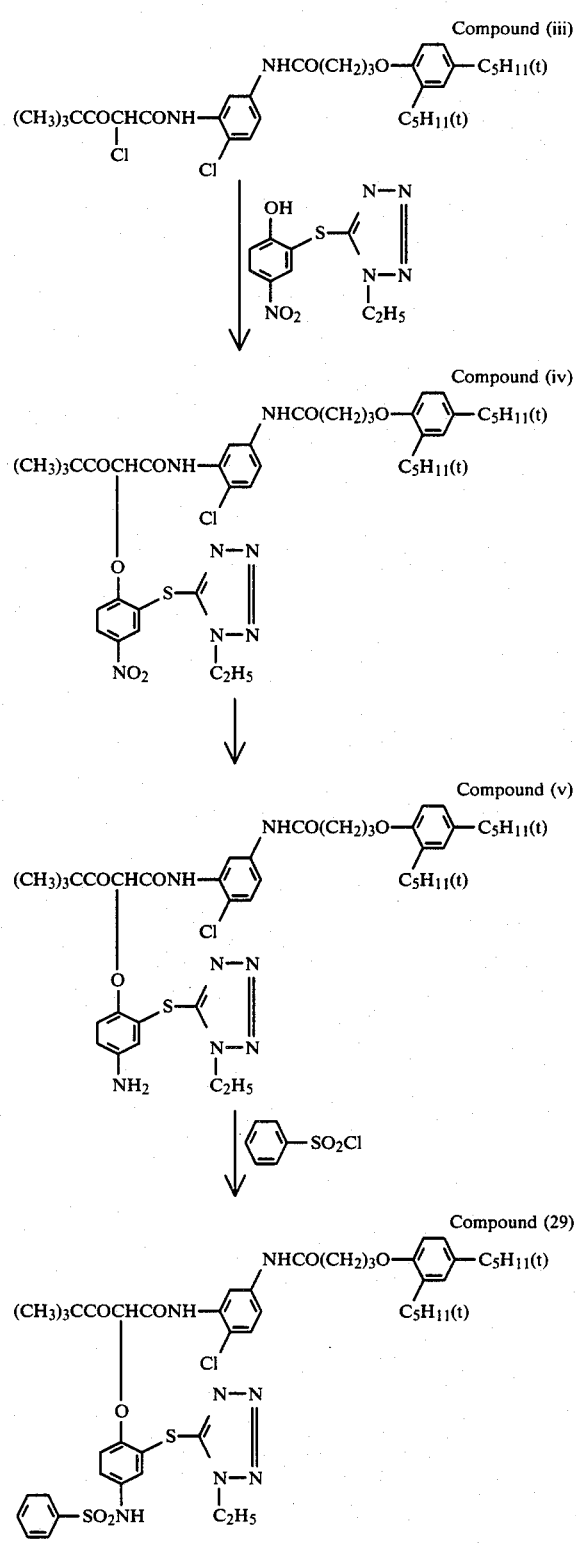

Step (1): Synthesis of Compound (iv)

A mixture of 30 g of Compound (iii), 7.5 ml of triethylamine, 14.6 g of 2-(2-hydroxy-5-nitrophenylthio)-1-ethyltetrazole and 200 ml of acetonitrile was reacted under refluxing for 3 hours. After the completion of the reaction, ethyl acetate was added to the reaction mixture and the mixture was placed in a separatory funnel and washed with water, diluted hydrochloric acid and then water in this order. The oil layer was separated, the solvent was distilled off and the residue thus-obtained was recrystallized from diethyl ether to obtain 28 g of the desired Compound (iv).

Step (2): Synthesis of Compound (v)

A mixture of 28 g of Compound (iv) obtained in Step (1) above, 20 ml of water, 20 ml of acetic acid and 200 ml of isopropanol was refluxed and then 20 g of iron powder divided into 5 parts was added dropwise thereto over a period of 30 minutes. After reacting for 30 minutes, the insoluble substance was removed by filtration, and the filtrate was poured into 300 ml of water with stirring. The crystals thus-deposited were collected by filtration to obtain Compound (V). After drying the weight of the compound was 25 g.

Step (3): Synthesis of Compound (29)

A mixture of 25 g of Compound (v) obtained in Step (2) above 5.3 g of benzenesulfonyl chloride, 5 ml of pyridine and 100 ml of chloroform was refluxed for 5 hours. After cooling to room temperature, the reaction mixture was placed in a separatory funnel and washed with water, dilute hydrochloric acid and then water in this order. The oil layer was separated, the solvent was distilled off under a reduced pressure and the residue thus-obtained was recrystallized from a solvent mixture of ethyl acetate and hexane to obtain 13 g of the desired Compound (29).

In order to incorporate the compounds according to the present invention and couplers to be used together into a silver halide emulsion layer known methods, including those described, e.g., in U.S. Pat. No. 2,322,027 can be used. For example, they can be dissolved in a solvent and then dispersed in a hydrophilic colloid. Examples of solvents usable for this process include organic solvents having a high boiling point, such as alkyl esters of phthalic acid (e.g., dibutyl phthalate, dioctyl phthalate, etc.), phosphoric acid esters (e.g., diphenyl phosphate, triphenyl phosphate, tricresyl phosphate, dioctyl butyl phosphate, etc.) citric acid esters (e.g., tributyl acetyl citrate, etc.), benzoic acid esters (e.g., octyl benzoate, etc.), alkylamides (e.g., diethyl laurylamides, etc.), esters of fatty acids (e.g., dibutoxyethyl succinate, dioctyl azelate, etc.), trimesic acid esters (e.g., tributyl trimesate, etc.), or the like; and organic solvents having a boiling point of from about 30° to about 150° C., such as lower alkyl acetates (e.g., ethyl acetate, butyl acetate, etc.), ethyl propionate, secondary butyl alcohol, methyl isobutyl ketone, β-ethoxyethyl acetate, methyl cellosolve acetate, or the like. Mixtures of organic solvents having a high boiling point and organic solvents having a low boiling point can also be used.

It is also possible to utilize the dispersing method using polymers, as described in Japanese Patent Publication No. 39853/76 and Japanese Patent Application (OPI) No. 59943/76.

Of the couplers, those having an acid group, such as a carboxylic acid group or a sulfonic acid group, can be introduced into hydrophilic colloids as an aqueous alkaline solution.

As the binder or the protective colloid for the photographic emulsion layers or intermediate layers of the photographic light-sensitive material of the present invention, gelatin is advantageously used, but other hydrophilic colloids can be used alone or together with gelatin.

As gelatin in the present invention, not only lime-processed gelatin, but also acid-processed gelatin may be employed. The methods for preparation of gelatin are described in greater detail in Ather Veis, *The Macromolecular Chemistry of Gelatin,* Academic Press (1964).

As the above-described hydrophilic colloids other than gelatin, it is possible to use proteins such as gelatin derivatives, graft polymers of gelatin and other polymers, albumin, casein, etc.; saccharides such as cellulose derivatives such as hydroxyethyl cellulose, carboxymethyl cellulose, cellulose sulfate, etc., sodium alginate, starch derivatives, etc.; and various synthetic hydrophilic high molecular weight substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinyl imidazole, polyvinylvinyl pyrazole, etc.

In the photographic emulsion layer of the photographic light-sensitive material used in the present invention, any of silver bromide, silver iodobromide, silver iodochlorobromide, silver chlorobromide and silver chloride may be used as the silver halide. A preferred silver halide is silver iodobromide containing 15 mol% or less of silver iodide. A silver iodobromide emulsion containing from 2 mol% to 12 mol% of silver iodide is particularly preferred.

Although the mean grain size of silver halide particles in the photographic emulsion (the mean grain size being determined with a grain diameter in those particles which are spherical or nearly spherical, and an edge length in those particles which are cubic as a grain size, and is expressed as a mean value calculated from projected areas) is not particularly limited, it is preferably 3μ or less.

The distribution of grain size may be broad or narrow.

Silver halide particles in the photographic emulsion may have a regular crystal structure, e.g., a cubic or octahedral structure, an irregular crystal structure, e.g., a spherical or plate-like structure, or a composite structure thereof. In addition, silver halide particles composed of those having different crystal structures may be used.

Further, the photographic emulsion wherein at least 50 percent of the total projected area of silver halide particles is super tabular silver halide particles having a diameter at least five times their thickness may be employed.

The inner portion and the surface layer of silver halide particles may be different in phase. Silver halide particles may be those in which a latent image is formed mainly on the surface thereof, or those in which a latent image is formed mainly in the interior thereof.

The photographic emulsion used in the present invention can be prepared in any suitable manner, e.g., by the methods as described in P. Glafkides, *Chimie et Physique Photographique,* Paul Montel (1967), G. F. Duffin, *Pho-* tographic Emulsion Chemistry, The Focal Press (1966), and V. L. Zelikman et al., Making and Coating Photographic Emulsion, The Focal Press (1964). That is, any of an acid process, a neutral process, an ammonia process, etc., can be employed.

Soluble silver salts and soluble halogen salts can be reacted by techniques such as a single jet process, A double jet process, and a combination thereof. In addition, there can be employed a method (so-called reversal mixing process) in which silver halide particles are formed in the presence of an excess of silver ions.

As one system of the double jet process, a so-called controlled double jet process in which the pAg in a liquid phase where silver halide is formed is maintained at a predetermined level can be employed. This process can produce a silver halide emulsion in which the crystal form is regular and the grain size is nearly uniform.

Two or more kinds of silver halide emulsions which are prepared separately may be used as a mixture.

The formation or physical ripening of silver halide particles may be carried out in the presence of cadmium salts, zinc salts, lead salts, thallium salts, iridium salts or its complex salts, rhodium salts or its complex salts, iron salts or its complex salts, and the like.

For removal of soluble salts from the emulsion after precipitate formation or physical ripening, a well known noodle washing process in which gelatin is gelated may be used. In addition, a flocculation process utilizing inorganic salts having a polyvalent anion (e.g., sodium sulfate), anionic surface active agents, anionic polymers (e.g., polystyrenesulfonic acid), or gelatin derivativs (e.g., aliphatic acylated gelatin, aromatic acrylated gelatin and aromatic carbamoylated gelatin) may be used.

Silver halide emulsions are usually chemically sensitized. For this chemical sensitization, for example, the methods as described in H. Frieser ed., Die Grundlagen Der Photographischen Prozesse mit Silberhalogeniden, Akademische Verlagsgesellschaft, pages 675 to 734 (1968) can be used. Namely, a sulfur sensitization process using active gelatin or compounds (e.g., thiosulfates, thioureas, mercapto compounds and rhodanines) containing sulfur capable of reacting with silver; a reduction sensitization process using reducing substances (e.g., stannous salts, amines, hydrazine derivatives, formamidinesulfinic acid, and silane compounds); a noble metal sensitization process using noble metal compounds (e.g., complex salts of Group VIII metals in the Periodic Table, such as Pt, Ir and Pd, etc., as well as gold complex salts); and so forth can be applied alone or in combination with each other.

The photographic emulsion used in the present invention may include various compounds for the purpose of preventing fog formation or of stabilizing photographic performance in the photographic light-sensitive material during the production, storage or photographic processing thereof. For example, those compounds known as antifoggants or stabilizers can be incorporated, including azoles such as benzothiazolium salts; nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particular 1-phenyl-5-mercaptotetrazole), etc.; mercaptopyrimidines; mercaptotriazines; thioketo compounds such as oxazolinethione, etc.; azaindenes such as triazaindenes, tetraazaindenes (particularly 4-hydroxy-substituted (1,3,3a,7)tetraazaindenes), pentaazaindenes, etc.; benzenethiosulfonic acids; benzenesulfinic acids; benzenesulfonic amides; etc.

In the photographic emulsion layers or other hydrophilic colloid layers of the photographic light-sensitive material of the present invention can be incorporated various surface active agents as coating aids or for other various purposes, e.g., prevention of charging, improvement of slipping properties, acceleration of emulsification and dispersion, prevention of adhesion, and improvement of photographic characteristics (for example, development acceleration, high contrast, and sensitization), etc.

Surface active agents which can be used are nonionic surface active agents, e.g., saponin (steroid-based), alkylene oxide derivatives (e.g., polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or polyalkylene glycol alkylamides, and silicone/polyethylene oxide adducts, etc.), glycidol derivatives (e.g., alkenylsuccinic acid polyglyceride and alkylphenol polyglyceride, etc.), fatty acid esters of polyhydric alcohols, and alkyl esters of sugar, etc.; anionic surface active agents containing an acidic group, such as a carboxy group, a sulfo group a phospho group, a sulfuric acid esters group, and a phosphoric acid ester group, for example, alkylcarboxylic acid salts, alkylsulfonic acid salts, alkylbenzenesulfonic acid salts, alkylnaphthalenesulfonic acid salts, alkylsufuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acid or aminoalkylphosphoric acid esters, alkylbetaines, and amine oxides; and cationic surface active agents, e.g., alkylamine salts, aliphatic or aromatic quaternary ammonium salts, heterocyclic quaternary ammonium salts (e.g., pyridinium and imidazolium), and aliphatic or heterocyclic phosphonium or sulfonium salts.

The photographic emulsion layer of the photographic light-sensitive material of the present invention may contain compounds such as polyalkylene oxide or its ether, ester, amine or like derivatives, thioether compounds, thiomorpholines, quaternary ammonium salt compounds, urethane derivatives, urea derivatives, imidazole derivatives, and 3-pyrazolidones for the purpose of increasing sensitivity or contrast, or of accelerating development.

In the photographic emulsion layer or other hydrophilic colloid layers of the photographic light-sensitive material of the present invention can be incorporated water-insoluble or sparingly soluble synthetic polymer dispersions for the purpose of improving dimensional stability, etc. Synthetic polymers which can be used include homo- or copolymers of alkyl acrylate or methacrylate, alkoxyalkyl acrylate or methacrylate, glycidyl acrylate or methacrylate, acrylamide or methacrylamide, vinyl esters (e.g., vinyl acetate), acrylonitrile, olefins, styrene, etc. and copolymers of the foregoing monomers and acrylic acid, methacrylic acid, $\alpha,\beta$-unsaturated dicarboxylic acid, hydroxyalkyl acrylate or methacrylate, sulfoalkyl acrylate or methacrylate, and styrenesulfonic acid, etc.

In photographic processing of layers composed of photographic emulsions in the photographic light-sensitive material of the present invention, any of known procedures and known processing solutions, e.g., those described in *Research Disclosure*, No. 176, pages 28 to 30 can be used. The processing temperature is usually chosen from between 18° C. and 50° C., although it may be lower than 18° C. or higher than 50° C.

Any fixing solutions which have compositions generally used can be used in the present invention. As fixing agents, thiosulfuric acid salts and thiocyanic acid salts, and in addition, organic sulfur compounds which are known to be effective as fixing agents can be used. These fixing solutions may contain water-soluble aluminum salts as hardeners.

Color developing solutions are usually alkaline aqueous solutions containing color developing agents. As these color developing agents, known primary aromatic amine developing agents, e.g., phenylenediamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc., can be used.

In addition, the compounds as described in L. F. A. Mason, *Photographic Processing Chemistry*, Focal Press, pages 226 to 229 (1966), U.S. Pat. Nos. 2,193,015 and 2,592,364, Japanese Patent Application (OPI) No. 64933/73, etc., may be used.

The color developing solutions can further contain pH buffering agents such as sulfite, carbonates, borates and phosphates of alkali metals, etc. developing inhibitors or anti-fogging agents such as bromides, iodides or organic anti-fogging agents, etc. In addition, if desired, the color developing solution can also contain water softeners; preservatives such as hydroxylamine, etc.; organic solvents such as benzyl alcohol, diethylene glycol, etc.; developing accelerators such as polyethylene glycol, quaternary ammonium salts, amines, etc.; dye forming couplers; competing couplers; fogging agents such as sodium borohydride, etc.; auxiliary developing agents such as 1-phenyl-3-pyrazolidone, etc.; viscosity-imparting agents; polycarbosylic acid type chelating agents; anti-oxidizing agents; and the like.

After color development, the photographic emulsion layer is usually bleached. This bleach processing may be performed simultaneously with a fix processing, or they may be performed independently.

Bleaching agents which can be used include compounds of polyvalent metals, e.g., iron (III), cobalt (III), chromium (VI), and copper (II), peracids, quinones and nitroso compounds. For example, ferricyanides; dichromates; organic complex salts of iron (III) or cobalt (III), e.g., complex salts of aminopolycarboxylic acids (e.g., ethylenediaminetetraacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol, etc. can be used. Of these compounds, potassium ferricyanide, iron (III) sodium ethylenediaminetetraacetate, and iron (III) ammonium ethylenediaminetetraacetate are particularly useful. Ethylenediaminetetraacetic acid iron (III) complex salts are useful in both an independent bleaching solution and a mono-bath bleach-fixing solution.

The photographic emulsion used in the present invention can also be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful.

Any conventionally utilized nuclei for cyanine dyes are applicable to these dyes as basic heterocyclic nuclei. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a qunioline nucleus, etc., are appropriate. The carbon atoms of these nuclei can also be substituted.

The merocyanine dyes and the complex merocyanine dyes that can be employed contain 5- or 6-membered heterocyclic nuclei such as a pyrazolin-5-one nucleus, a thiohydantoin nucleus, a 2-thioxazolidin-2,4-dione nucleus, a thiazolidine-2,4-dione nucleus, a rhodanine nucleus, a thiobarbituric acid nucleus, and the like.

These sensitizing dyes can be employed individually, and can also be employed in combination. A combination of sensitizing dyes is often used particularly for the purpose of supersensitization.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present.

The present invention is also applicable to a multi-layer multicolor photographic material containing layers sensitive to at least two different spectral wavelength ranges on a support. A multi layer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

The same or different photographic emulsion layers or light-insensitive layers of the photographic light-sensitive material of the present invention can be incorporated, in addition to the compounds according to the present invention described above, with other dye forming couplers, i.e., compounds capable of forming color upon oxidative coupling with aromatic primary amine developing agents (e.g., phenylenediamine derivatives, aminophenol derivatives, etc.) during the course of color development processing. Examples of such couplers include magenta couplers, such as 5-pyrazolone couplers, pyrazolobenzimidazole couplers, pyrazoloimidazole couplers, pyrazolopyrazole couplers, pyrazolotriazole couplers, pyrazolotetrazole couplers, cyanoacetyl coumarone couplers and open chain acylacetonitrile couplers, etc.; yellow couplers, such as acylacetamide couplers (e.g., benzoylacetanilides, pivaloylacetanilides, etc.), etc.; and cyan couplers, such as naphthol couplers and phenol couplers, etc. It is preferable to use non-diffusible couplers containing a hydrophobic group (so-called ballast group) with the molecule or polymeric couplers. They may be either 4-equivalent or 2-equivalent with respect to silver ions. It is also possible to use colored couplers capable of exerting color correction effects, or couplers capable of releasing development inhibitors during the course of development (so-called DIR couplers).

Further, the emulsion layer may contain non-color-forming DIR coupling compounds which release a development inhibitor, the product of which formed by a coupling reaction is colorless, other than DIR couplers.

Moreover, the photographic light-sensitive material may contain compounds which release a development inhibitor during the course of development, other than DIR couplers.

Two or more kinds of the couplers according to the present invention and the above-described couplers and the like can be incorporated together in the same layer for the purpose of satisfying the properties required of the photographic light-sensitive material, or the same compound can naturally be added to two or more layers.

The photographic light-sensitive material of the present invention may contain inorganic or organic hardeners in the photographic emulsion layer and other hydrophilic colloid layers thereof. For example, chromium salts (e.g., chromium alum, chromium acetate, etc.) aldehydes (e.g., formaldehyde, glyoxal, glutaraldehyde, etc.), N-methylol compounds (e.g., dimethylolurea, methyloldimethylhydantoin, etc.) dioxane derivatives (e.g., 2,3-dihydroxydioxane, etc.), active vinyl compounds (e.g., 1,3,5-triacryloylhexahydroso-triazine, 1,3-vinylsulfonyl-2-propanol, etc.), active halogen compounds (e.g., 2,4-dichloro-6-hydroxy-s-triazine, etc.), and mucohalogenic acids (e.g., mucochloric acid, mucophenoxychloric acid, etc.) can be used alone or in combination with each other.

In the photographic light-sensitive material of the invention, when dyes, ultraviolet ray absorbing agents, and the like are incorporated in the hydrophilic colloid layers, they may be mordanted with cationic polymers, etc.

The photographic light-sensitive material of the present invention may contain therein hydroquinone derivatives, aminophenol derivatives, gallic acid derivatives, ascorbic acid derivatives, etc., as color fog preventing agents.

The hydrophilic colloid layers of the photographic light-sensitive material of the present invention can contain ultraviolet ray absorbing agents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,705,805 and 3,707,375), butadiene compounds (e.g., those described in U.S. Pat. No. 4,045,229) or benzoxazole compounds (e.g., those described in U.S. Pat. No. 3,700,455) can be employed. Ultraviolet ray absorbing couplers (e.g., α-naphthol type cyan dye forming couplers) and ultraviolet ray absorbing polymers can also be employed. These ultraviolet rays absorbing agents can also be mordanted in a specific layer(s), if desired.

The photographic light-sensitive material of the present invention may contain water-soluble dyes in the hydrophilic colloid layers thereof as filter dye or for various purposes, e.g., irradiation prevention. Examples of such dyes include oxonol dyes, hemioxonol dyes, styryl dyes, merocyanine dyes, cyanine dyes, and azo dyes. In particular, oxonol dyes, hemioxonol dyes, and merocyanine dyes are useful.

In carrying out the present invention, known color fading preventing agents can be used together. Color image stavilizers can be used alone or in combination with each other. Typical known color fading preventing agents include hydroquinone derivatives, gallic acid derivatives, p-alkoxyphenols, p-oxyphenol derivatives, and bisphenols, etc.

The present invention will be explained in greater detail with reference to the following examples, but the present invention should not be construed as being limited thereto. Unless otherwise specified all percents, ratios, etc. are by weight.

EXAMPLE 1

On a cellulose triacetate film support provided with a subbing layer was coated Coating Solution A described below so as to result in a silver amount of 2.0 g/m² and a protective layer was applied to the resulting emulsion layer to prepare Sample A.

Coating Solution A 100 g of a cyan coupler, i.e., 2-(heptafluorobutyramido)-5-[2'-(2'',4''-di-tert-amylphenoxy)-butyramido]phenol (main coupler) was dissolved in 100 ml of tricresyl phosphate and 100 ml of ethyl acetate and stirred at a high speed together with 1 kg of a 10% aqueous gelatin solution to prepare an emulsion. Then, 500 g of the emulsion thus-obtained was mixed with 1 kg of a red-sensitive silver iodobromide emulsion (containing 50 g of silver and 60 g of gelatin, and having an iodide content 5 mol%) and to the mixture was added 50 ml of a 2% aqueous solution of 2-hydroxy-4,6-dichloro-s-triazine sodium salt as a gelatin hardener to prepare Coating Solution A.

The protective layer was prepared by coating a 5% aqueous gelatin solution so as to result in a dry thickness of 1μ.

Samples B to H were prepared in the same manner as described in Sample A except that an amount of the main coupler was reduced to 90 g and that the coupler shown in Table 1 below was further added in an amount of 20 mol% of the main coupler to Coating Solution A.

These samples thus-obtained were exposed to white light for sensitometry, for determination of sharpness or for determination of graininess and then subjected to the development processing as described below.

The comparative coupler used in this example had the following structure.

Comparative Coupler (a)

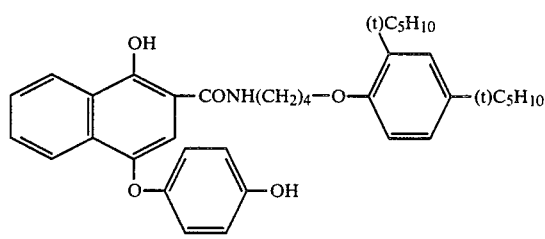

The development processing was carried out according to the following steps.

| Processing Steps | Time | Temperature |
|---|---|---|
| First development | 6 min | 38 ± 0.3° C. |
| Washing with water | 2 min | " |
| Reversal | 2 min | " |
| Color development | 6 min | " |
| Conditioning | 2 min | " |
| Bleaching | 6 min | " |
| Fixing | 4 min | " |
| Washing with water | 4 min | " |
| Stabilizing | 1 min | ordinary temperature |
| Drying | | |

The composition of each processing solution used in the above described processing is as follows.

First Development Bath

| | |
|---|---|
| Water | 700 ml |
| Sodium tetrapolyphosphate | 2 g |
| Sodium sulfite | 20 g |
| Hydroquinone monosulfonate | 30 g |
| Sodium carbonate (monohydrate) | 30 g |
| 1-Phenyl-4-methyl-4-methoxy-3-pyrazolidone | 2 g |
| Potassium bromide | 2.5 g |
| Potassium thiocyanate | 1.2 g |
| Potassium iodide (0.1% solution) | 2 ml |
| Water to make | 1,000 ml |

Reversal Bath

| | |
|---|---|
| Water | 700 ml |
| 6 Na Salt of nitrilo-N,N,N—trimethylenephosphonic acid | 3 g |
| Stannous chloride (dihydrate) | 1 g |
| p-Aminophenol | 0.1 g |
| Sodium hydroxide | 8 g |
| Glacial acetic acid | 15 ml |
| Water to make | 1,000 ml |

Color Development Bath

| | |
|---|---|
| Water | 700 ml |
| Sodium tetrapolyphosphate | 2 g |
| Sodium sulfite | 7 g |
| Sodium tertiary phosphate (dihydrate) | 36 g |
| Potassium bromide | 1 g |
| Potassium iodide (0.1% solution) | 90 ml |
| Sodium hydroxide | 3 g |
| Citrazinic acid | 1.5 g |

-continued

| | |
|---|---|
| 4-Amino—3-methyl-N—ethyl-N—$\beta$-hydroxyethyl-aniline sesquisulfate monohydrate | 11 g |
| Ethylenediamine | 3 g |
| Water to make | 1,000 ml |

Conditioning Bath

| | |
|---|---|
| Water | 700 ml |
| Sodium sulfite | 12 g |
| Sodium ethylenediaminetetraacetate (dihydrate) | 8 g |
| Thioglycerol | 0.4 ml |
| Glacial acetic acid | 3 ml |
| Water to make | 1,000 ml |

Bleaching Bath

| | |
|---|---|
| Water | 800 ml |
| Sodium ethylenediaminetetraacetate (dihydrate) | 2.0 g |
| Iron (III) ammonium ethylenediamine-tetraacetate (dihydrate) | 120.0 g |
| Potassium bromide | 100.0 g |
| Water to make | 1,000 ml |

Fixing Bath

| | |
|---|---|
| Water | 800 ml |
| Ammonium thiosulfate | 80.0 g |
| Sodium sulfite | 5.0 g |
| Sodium bisulfite | 5.0 g |
| Water to make | 1,000 ml |

Stabilizing Bath

| | |
|---|---|
| Water | 800 ml |
| Formalin (37 wt %) | 5.0 ml |
| Fuji Drywel | 5.0 ml |
| Water to make | 1,000 ml |

With the samples thus-processed optical density, sensitivity, sharpness and graininess were measured and the results shown in Table 1 below were obtained.

TABLE 1

| Sample | | Additional Coupler | Maximum Density | Minimum Density | Sharpness (10 cycles/mm) | Graininess (Density of 0.5) |
|---|---|---|---|---|---|---|
| A | (Comparison) | none | 3.04 | 0.15 | 102 | 0.0185 |
| B | (Present Invention) | (1) | 2.90 | 0.14 | 116 | 0.0138 |
| C | (Present Invention) | (2) | 2.88 | 0.14 | 115 | 0.0141 |
| D | (Present Invention) | (3) | 2.90 | 0.14 | 117 | 0.0148 |
| E | (Present Invention) | (4) | 2.87 | 0.14 | 115 | 0.0150 |
| F | (Present Invention) | (5) | 2.92 | 0.14 | 114 | 0.0142 |
| G | (Present Invention) | (6) | 2.91 | 0.14 | 117 | 0.0145 |
| H | (Comparison) | (a) | 2.95 | 0.14 | 107 | 0.0170 |

The sharpness was evaluated using the MTF value at 10 cycles/mm.
The graininess was evaluated using the RMS value at density of 0.5.

From the results shown in Table 1 above it is apparent that the couplers according to the present invention improve the sharpness and graininess and the degree of improvement is great in comparison with the known coupler.

EXAMPLE 2

On a cellulose triacetate film support provided with a subbing layer was coated Coating Solution B described below so as to result in a silver amount of 2.0 g/m² and the same protective layer as described in Example 1 was applied to the resulting emulsion layer to prepare Sample I.

Coating Solution B 100 g of a magenta coupler, i.e., 1-(2,4,6-trichlorophenyl)-3-{3-[2-(2,4-di-tert-amylphenoxy)butyramido]-benzamido}-5-oxo-2-pyrazoline (main coupler) was dissolved in 100 ml of tricresyl phosphate and 100 ml of ethyl acetate and stirred at a high speed together with 1 kg of a 10% aqueous gelatin solution to prepare an emulsion. Then, 500 g of the emulsion thus-obtained was mixed with 1 kg of a green sensitive silver iodobromide emulsion (containing 50 g of silver and 60 g of gelatin, and having an iodide content of 5 mol%) and to the mixture was added 50 ml of a 2% aqueous solution of 2-hydroxy-4,6-dichloro-s-triazine sodium salt as a gelatin hardener to prepare Coating Solution B.

Samples J and K were prepared in the same manner as described in Sample I except that an amount of the main coupler was reduced to 90 g and that the coupler shown in Table 2 below was further added in an amount of 20 mol% of the main coupler to Coating Solution B.

Samples I to K thus-obtained were exposed to light and processed in the same manner as described in Example 1, and the results shown in Table 2 below were obtained by the measurement using green light.

TABLE 2

| Sample | | Additional Coupler | Maximum Density | Minimum Density | Sharpness (10 cycles/mm) | Graininess (Density of 0.5) |
|---|---|---|---|---|---|---|
| I | (Comparison) | none | 2.95 | 0.15 | 103 | 0.0210 |
| J | (Present Invention) | (13) | 2.83 | 0.13 | 114 | 0.0167 |
| K | (Present Invention) | (20) | 2.86 | 0.13 | 116 | 0.0172 |

From the results shown in Table 2 above it is apparent that the couplers according to the present invention can remarkably improve the sharpness and graininess when they are incorporated into photographic light-sensitive materials.

EXAMPLE 3

On a cellulose triacetate film support provided with a subbing layer was coated Coating Solution C described below so as to result in a silver amount of 2.0 g/m² and the same protective layer as described in Example 1 was applied to the resulting emulsion layer to prepare Sample L.

Coating Solution C 100 g of a yellow coupler, i.e. α-pivaloyl-α-(1-benzyl-5-ethoxy-3-hydantoinyl)-2-chloro-5-dodecyloxycarbonylacetanilide (main coupler) was dissolved in 100 ml of dibutyl phthalate and 100 ml of ethyl acetate and stirred at a high speed together with 1 kg of a 10% aqueous gelatin solution to prepare an emulsion. Then, 500 g of the emulsion thus-obtained was mixed with 1 kg of a blue sensitive silver iodobromide emulsion (containing 50 g of silver and 60 g of gelatin, and having an iodide content 5 mol%) and to the mixture was added 50 ml of a 2% aqueous solution of 2-hydroxy-4,6-dichloro-s-triazine sodium salt as a gelatin hardener to prepare Coating Solution C.

Samples M and N were prepared in the same manner as described in Sample L except that the amount of the main coupler was reduced to 90 g and that the coupler shown in Table 3 below was further added in an amount of 20 mol% of the main coupler to Coating Solution C.

Samples L to N thus-obtained were exposed to light and processed in the same manner as described in Example 1, and the results shown in Table 3 below were obtained by the measurements using blue light.

TABLE 3

| Sample | | Additional Coupler | Maximum Density | Minimum Density | Sharpness (10 cycles/mm) | Graininess (Density of 0.5) |
|---|---|---|---|---|---|---|
| L | (Comparison) | none | 2.70 | 0.12 | 103 | 0.0270 |
| M | (Present Invention) | (8) | 2.54 | 0.11 | 115 | 0.0205 |
| N | (Present Invention) | (15) | 2.52 | 0.11 | 117 | 0.0197 |

From the results shown in Table 3 above it is apparent that the couplers according to the present invention have excellent properties with respect to the sharpness and graininess.

EXAMPLE 4

Samples A to N as described in Examples 1 to 3 above were exposed to light in the same manner as described in Example 1 and then subjected to the development processing which was carried out at 38° C. according to the following processing steps.

| Processing Steps | Time |
|---|---|
| 1. Color development | 3 min and 15 sec |
| 2. Bleaching | 6 min and 30 sec |
| 3. Washing with water | 3 min and 15 sec |
| 4. Fixing | 6 min and 30 sec |
| 5. Washing with water | 3 min and 15 sec |
| 6. Stabilizing | 3 min and 15 sec |

The composition of each processing solution used in the above-described processing steps is as follows.

| Color Developing Solution | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-N—β-hydroxyethylamino)-2-methylaniline sulfate | 4.5 g |
| Water to make | 1 l |
| Bleaching Solution | |
| Ammonium bromide | 160.0 g |
| Aqueous ammonia (28%) | 25.0 ml |
| Sodium ethylenediaminetetraacetato iron (III) | 130.0 g |
| Glacial acetic acid | 14.0 ml |
| Water to make | 1 l |
| Fixing Solution | |
| Sodium tetrapolyphosphate | 2.0 g |
| Sodium sulfite | 4.0 g |
| Ammonium thiosulfate aqueous solution (70%) | 175.0 ml |
| Sodium bisulfite | 4.6 g |
| Water to make | 1 l |
| Stabilizing Solution | |
| Formalin | 8.0 ml |
| Water to make | 1 l |

The results thus-obtained were almost the same as those obtained in Examples 1 to 3 and illustrated that the couplers according to the present invention can exhibit their excellent properties when they were subjected to the color negative processing.

EXAMPLE 5

On a triacetyl cellulose support provided with a subbing layer were coated, in order, the emulsion layers and subsidiary layers as described below to prepare Sample 501.

First Layer: Low Sensitive Red-Sensitive Emulsion Layer 100 g of a cyan coupler, i.e., 2-(heptafluorobutyramido)-5-[2'-(2'',4''-di-tert-amylphenoxy)-butyramido]phenol was dissolved in 100 ml of tricresyl phosphate and 100 ml of ethyl acetate and stirred at a high speed together with 1 kg of a 10% aqueous gelatin solution to prepare an emulsion. Then, 500 g of the emulsion thus-obtained was mixed with 1 kg of a low-sensitive red-sensitive silver iodobromide emulsion spectrally sensitized with Sensitizing Dye A (containing 70 g of silver and 60 g of gelatin, and having an iodide content of 6 mol% and the grain size distribution wherein 81% of the total number of silver halide grains have a size within the range of the mean grain size ±40%), and the resulting mixture was then coated so as to result in a dry thickness of $2\mu$ (silver amount: 0.5 g/m$^2$).

Second Layer: Medium Sensitive Red-Sensitive Emulsion Layer 100 g of a cyan coupler, i.e., 1-(heptafluorobutyramido)-5-[2'-(2'-(2'',4''-di-tert-amylphenoxy)butyramido]phenol was dissolved in 100 ml of tricresyl phosphate and 100 ml of ethyl acetate and stirred at a high speed together with 1 kg of a 10% aqueous gelatin solution to prepare an emulsion. Then, 1,000 g of the emulsion thus-obtained was mixed with 1 kg of a medium-sensitive red-sensitive silver iodobromide emulsion spectrally sensitized with Sensitizing Dye A (containing 70 g of silver and 60 g gelatin, and having an iodide content of 6 mol% and 76% of the grain size distribution as defined in the emulsion of the First Layer), and the resulting mixture was then coated so as to result in a dry thickness of $1\mu$ (silver amount: 0.4 g/m$^2$).

Third Layer: High Sensitive Red-Sensitive Emulsion Layer 100 g of a cyan coupler, i.e., 2-(heptafluorobutyramido)-5-[2'-(2'',4''-di-tert-amylphenoxy)-butyramido]phenol was dissolved in 100 ml of tricresyl phosphate and 100 ml of ethyl acetate and stirred at a high speed togehter with 1 kg of a 10% aqueous gelatin solution to prepare an emulsion. Then, 1,000 g of the emulsion thus-obtained was mixed with 1 kg of a high-sensitive red-sensitive silver iodobromide emulsion spectrally sensitized with Sensitizing Dye A (containing 70 g of silver and 60 g gelatin, and having an iodide content of 6 mol% and 78% of the grain size distribution as defined above), and the resulting mixture was then coated so as to result in a dry thickness of $1\mu$ (silver amount: 0.4 g/m$^2$).

Fourth Layer: Intermediate Layer 50 g of 2,5-di-tert-octylhydroquinone was dissolved in 100 ml of dibutyl phthalate and 100 ml of ethyl acetate, and stirred at a high speed together with 1 kg of a 10% aqueous gelatin solution to prepare an emulsion. Then, 1 kg of the emulsion thus-obtained was mixed with 1 kg of a 10% aqueous gelatin solution, and the resulting mixture was coated so as to result in a coating amount of the 2,5-di-tert-octylhydroquinone being 200 mg/m$^2$.

Fifth Layer: Low sensitive Green-Sensitive Emulsion Layer

An emulsion was prepared in the same manner as described in the preparation of the emulsion for the first layer except that a magenta coupler, i.e., 1-(2,4,6-trichlorophenyl)-3-[3-(2,4-di-tert-amylphenoxyacetamido)=benzamido]-5-pyrazolone, was used in place of the cyan coupler. Then, 500 g of the emulsion thus-obtained was mixed with 1 kg of a green-sensitive, low-sensitive silver iodobromide emulsion spectrally sensitized with Sensitizing Dyes B and C (molar ratio of B/C: 0.5) (containing 70 g of silver and 60 g of gelatin, and having an iodide content of 5.2 mol% and 81% of the grain size distribution as defined above), and the resulting mixture was coated so as to result in a dry thickness of $2.0\mu$ (silver amount: 0.7 g/m$^2$).

Sixth Layer: Medium Sensitive Green-Sensitive Emulsion Layer

An emulsion was prepared in the same manner as described in the preparation of the emulsion for the first layer except that a magenta coupler, i.e., 1-(2,4,6-trichlorophenyl)-3-[3-(2,4-di-tert-amylphenoxyacetamido)benzamido]-5-pyrazolone, was used in place of the cyan coupler. Then, 1,000 g of the emulsion thus-obtained was mixed with 1 kg of a green-sensitive, medium-sensitive silver iodobromide emulsion spectrally sensitized with Sensitizing Dyes E and C (molar ratio of B/C: 0.5) (containing 70 g of silver and 60 g of gelatin, and having an iodide content of 5.2 mol% and 75% of the grain size distribution as defined above), and the resulting mixture was coated so as to result in a dry thickness of $1\mu$ (silver amount: 0.35 g/m$^2$).

Seventh Layer: High Sensitive Green-Sensitive Emulsion Layer

An emulsion was prepared in the same manner as described in the preparation of the emulsion for the first layer except that a magenta coupler, i.e., 1-(2,4,6-trichlorophenyl)-3-[3-(2,4-di-tert-amylphenoxyacetamido)benzamide]-5-pyrazolone, was used in place of the cyan coupler. Then, 1,000 g of the emulsion thus-obtained was mixed with 1 kg of a green-sensitive, high-sensitive silver iodobromide emulsion spectrally sensitized with Sensitizing Dyes B and C (molar ratio of B/C: 0.5) (containing 70 g of silver and 60 g of gelatin, and having an iodide content of 5.2 mol% and 75% of the grain size distribution as defined above), and the resulting mixture was coated so as to result in a dry thickness of $1\mu$ (silver amount: 0.35 g/m$^2$).

Eight Layer: Intermediate Layer 1 kg of the emulsion used in the preparation of the fourth layer was mixed with 1 kg of a 10% aqueous gelatin solution and coated so as to result in a dry thickness of $1\mu$.

Ninth Layer: Yellow Filter Layer

An emulsion containing yellow colloidal silver was coated so as to result in a dry thickness of $1\mu$.

Tenth Layer: Low Sensitive Blue-Sensitive Emulsion Layer

An emulsion was prepared in the same manner as described in the preparation of the emulsion for the first layer except that a yellow coupler, i.e., α-pivaloyl-α-(1-benzyl-5-ethoxy-3-hydantoinyl)-2-chloro-5-dodecyloxy-carbonylacetanilide, was used in place of the cyan coupler. Then, 1,000 g of the emulsion thus-obtained was mixed with 1 kg of a blue-sensitive, low-sensitive silver iodobromide emulsion (containing 70 g of silver and 60 g of gelatin and having an iodide content of 5.5 mol% and 77% of the grain size distribution as defined above), and the resulting mixture was coated so as to result in a dry thickness of 2.0μ (silver amount: 0.6 g/m$^2$).

Eleventh Layer: Medium Sensitive Blue-Sensitive Emulsion Layer

An emulsion was prepared in the same manner as described in the preparation of the emulsion for the first layer except that a yellow coupler, i.e., α-pivaloyl-α-(1-benzyl-5-ethoxy-3-hydantoinyl)-2-chloro-5-dodecyloxycarbonylacetanilide, was used in place of the cyan coupler. Then, 1,000 g of the emulsion thus-obtained was mixed with 1 kg of a blue-sensitive, medium-sensitive silver iodobromide emulsion (containing 70 g of gelatin and 60 g of gelatin and having an iodide content of 5.5 mol% and 72% of the grain size distribution as defined above), and the resulting mixture was coated so as to result in a dry thickness of 1.0μ (silver amount: 0.5 g/m$^2$).

Twelfth Layer: High Sensitive Blue-Sensitive Emulsion Layer

An emulsion was prepared in the same manner as described in the preparation of the emulsion for the first layer except that a yellow coupler, i.e., α-pivaloyl-α-(1-benzyl-5-ethoxy-3-hydantoinyl)-2-chloro-5-dodecyloxycarbonylacetanilide, was used in place of the cyan coupler. Then, 1,000 g of the emulsion thus-obtained was mixed with 1 kg of a blue sensitive, high-sensitive silver iodobromide emulsion (containing 70 g of gelatin and 60 g of gelatin and having an iodide content of 5.5 mol% and 72% of the grain size distribution as defined above), and the resulting mixture was coated so as to result in a dry thickness of 1.0μ (silver amount: 0.5 g/m$^2$).

Thirteenth Layer: Second Protective Layer 1 kg of the emulsion used in the proparation of the fourth layer was mixed with 1 kg of a 10% aqueous gelatin solution and coated so as to result in a dry thickness of 2μ.

Fourteenth Layer: First Protective Layer

A 10% aqueous gelatin solution containing a fine grain silver iodobromide emulsion which had not been chemically sensitized (grain size: 0.15μ; 1 mol% silver iodobromide emulsion) was coated so that the amount of silver coated was 0.3 g/m$^2$ and the dry thickness was 1μ.

The spectral sensitizing dyes used in the preparation of Sample 501 had the following structures.

Sensitizing Dye A:

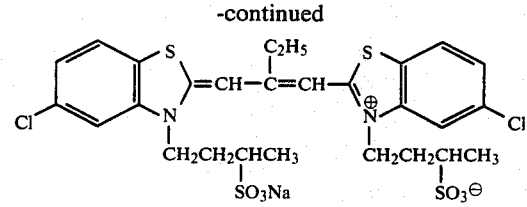

Sensitizing Dye B:

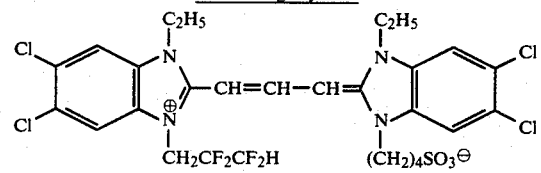

Sensitizing Dye C:

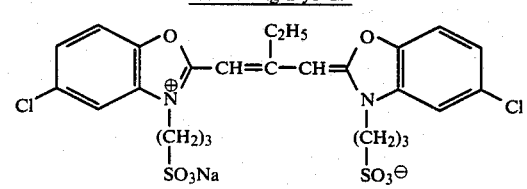

Sample 502 was prepared in the same manner as described in Sample 501 except that each of the cyan couplers used in the first layer to the third layer was changed to a mixture of the the cyan coupler and Coupler (1) according to the present invention in a molar ratio of 8:2 and that coating amounts of the first layer to the third layer were increased so as to result in the same gradation as in Sample 501.

Sample 503 was prepared in the same manner as described in Sample 501 except that each of the magenta couplers used in the fifth layer to the seventh layer was changed to a mixture of the magenta coupler and Coupler (13) according to the present invention in a molar ratio of 8:2 and that coating amounts of the fifth layer to the seventh layer were increased so as to result in the same gradation as in Sample 501.

Sample 504 was prepared in the same manner as described in Sample 501 except that each of the yellow couplers used in the tenth layer to twelfth layer was changed to a mixture of the yellow coupler and Coupler (23) according to the present invention in a molar ratio of 8:2 and that the coating amount of the tenth layer to the twelfth layer was increased so as to result in the same gradation as in Sample 501.

Samples 501 to 504 thus-obtained were exposed to light and processed in the same manner as described in Example 1 and then the sharpness and graininess of these samples were measured. It was found that Samples 502 to 504 each containing the couplers according to the present invention had excellent sharpness and graininess in comparison with Sample 501.

EXAMPLE 6

Samples 501 and 502 as described in Example 5 above were exposed stepwise to red light and then exposed uniformly to blue light. These samples were processed in the same manner as described in Example 1. The samples thus-processed were subjected to sensitometry with red light and blue light, and the densities were measured by blue light at the areas where the maximum density and the minimum density were obtained by the measurement with red light. The results thus-obtained are shown in Table 4 below.

TABLE 4

| Sample | Density to Blue Light | |
|---|---|---|
| | At Maximum Red Light Density | At Minimum Red Light Density |
| 501 | 2.90 | 2.95 |
| 502 | 2.57 | 2.92 |

From the results shown in Table 4 above it is apparent that the color formation in the blue-sensitive layers is restrained at the areas where the color density of the red-sensitive layers is high in Sample 502 containing the couplers according to the present invention. This fact indicates that the development inhibiting effects, that is, the interlayer effects of the red-sensitive layer to the blue-sensitive layer are generated.

EXAMPLE 7

On a polyethylene terephthalate film support were coated layers having the compositions set forth below to prepare a multilayer color photographic light-sensitive material.

First Layer: Antihalation Layer

A gelatin layer containing black colloidal silver

Second Layer: Intermediate Layer

A gelatin layer containing a dispersion of 2,5-di-tert-octylhydroquinone

Third Layer: First Red-Sensitive Emulsion Layer

A silver iodobromide emulsion (iodide content: 5 mol%), silver coated amount: 1.8 g/m²

| | |
|---|---|
| Sensitizing Dye I | $4.5 \times 10^{-4}$ mol per mol of silver |
| Sensitizing Dye II | $1.5 \times 10^{-4}$ mol per mol of silver |
| Coupler EX-1 | 0.03 mol per mol of silver |
| Coupler EX-3 | 0.003 mol per mol of silver |
| Coupler (34) of Invention | 0.003 mol per mol of silver |

Fourth Layer: Second Red-Sensitive Emulsion Layer

A silver iodobromide emulsion (iodide content: 10 mol%), silver coated amount: 1.4 g/m²

| | |
|---|---|
| Sensitizing Dye I | $3 \times 10^{-4}$ mol per mol of silver |
| Sensitizing Dye II | $1 \times 10^{-4}$ mol per mol of silver |
| Coupler EX-1 | 0.002 mol per mol of silver |
| Coupler EX-2 | 0.02 mol per mol of silver |
| Coupler EX-3 | 0.0016 mol per mol of silver |

Fifth Layer: Intermediate Layer

Same as the Second Layer

Sixth Layer: First Green-Sensitive Emulsion Layer

A silver iodobromide emulsion (iodide content: 6 mol%), silver coated amount: 1.8 g/m²

| | |
|---|---|
| Sensitizing Dye III | $5 \times 10^{-4}$ mol per mol of silver |
| Sensitizing Dye IV | $2 \times 10^{-4}$ mol per mol of silver |
| Coupler EX-4 | 0.05 mol per mol of silver |
| Coupler EX-5 | 0.008 mol per mol of silver |
| Coupler EX-9 | 0.0015 mol per mol of silver |

Seventh Layer: Second Green-Sensitive Emulsion Layer

A silver iodobromide emulsion (iodide content: 8 mol%), silver coated amount: 1.3 g/m²

| | |
|---|---|
| Sensitizing Dye III | $3 \times 10^{-4}$ mol per mol of silver |
| Sensitizing Dye IV | $1.2 \times 10^{-4}$ mol per mol of silver |
| Coupler EX-7 | 0.017 mol per mol of silver |
| Coupler EX-6 | 0.003 mol per mol of silver |
| Coupler EX-10 | 0.0003 mol per mol of silver |

Eighth Layer: Yellow Filter Layer

A gelatin layer containing a dispersion of yellow colloidal silver and 2,5-di-tert-octylhydroquinone Ninth Layer: First Blue-Sensitive Emulsion Layer A silver iodobromide emulsion (iodide content: 6 mol%), silver coated amount: 0.7 g/m²

| | |
|---|---|
| Coupler EX-8 | 0.25 mol per mol of silver |
| Coupler EX-9 | 0.015 mol per mol of silver |

Tenth Layer: Second Blue-Sensitive Emulsion Layer

A silver iodobromide emulsion (iodide content: 6 mol%), silver coated amount: 0.6 g/m²

| | |
|---|---|
| Coupler EX-8 | 0.06 mol per mol of silver |

Eleventh Layer: First Protective Layer

A gelatin layer containing silver iodobromide (iodide content: 1 mol%, average particle size: 0.07μ, silver coated amount: 0.5 g/m²) and a dispersion of Ultraviolet Ray Absorbing agent UV-1.

Twelfth Layer: Second Protective Layer

A gelatin layer containing polymethyl methacrylate particles (having a diameter of about 1.5μ)

Gelatin Hardener H-1 and a surface active agent were incorporated into each of the layers in addition to the above-described components.

The sample thus-prepared was designated Sample 101.

Preparation of Samples 102 to 109

Samples 102 to 109 were prepared in the same manner as described for Sample 101 except changing Coupler (34) used in the low-sensitive red-sensitive emulsion layer to the compounds as shown in Table 5 below, respectively.

The structures of the compounds used for preparing these samples are as follows:

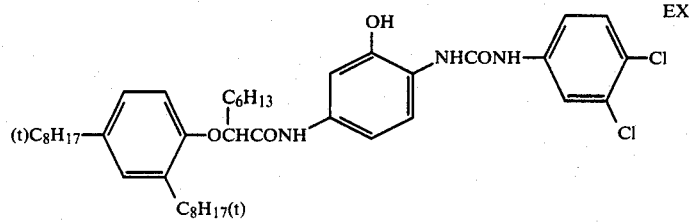
EX-1
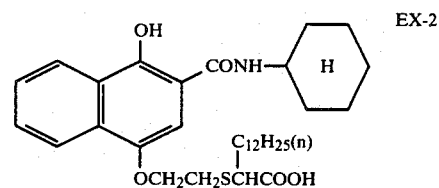
EX-2
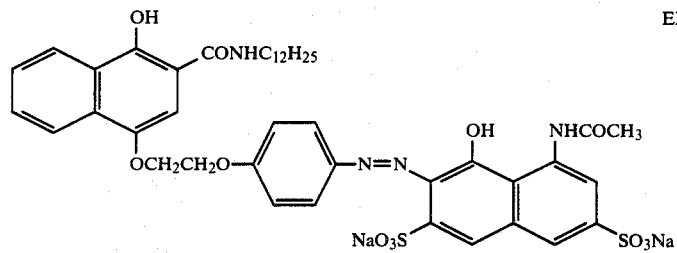
EX-3
n/m + m' = 1 (weight ratio)
m/m' = 1 (weight ratio)
molecular weight: about 40,000
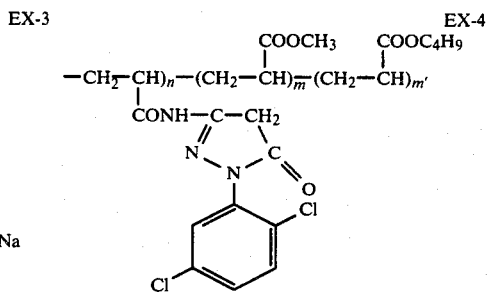
EX-4
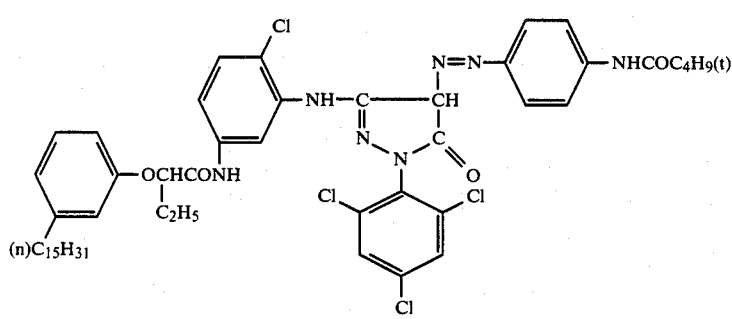
EX-5
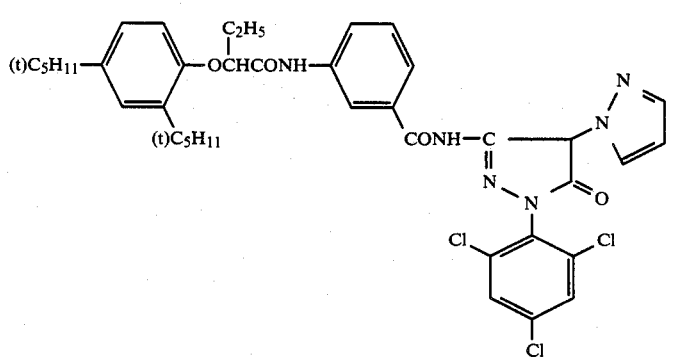
EX-6
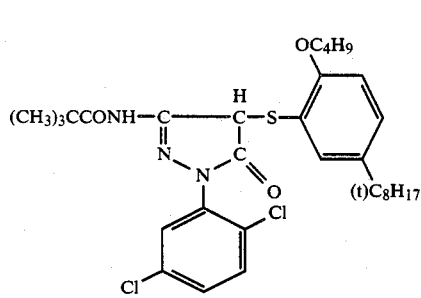
EX-7
wherein (t)C$_8$H$_{17}$ is (CH$_3$)$_3$CCH$_2$C(CH$_2$)$_2$—.
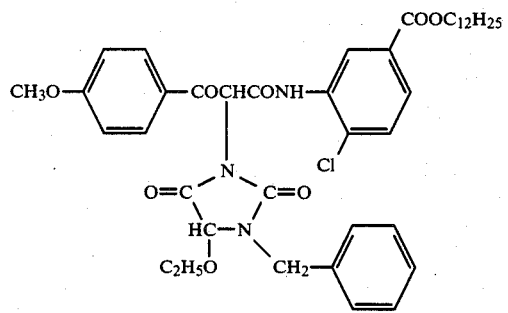
EX-8

-continued
EX-9
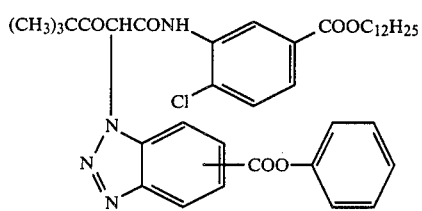
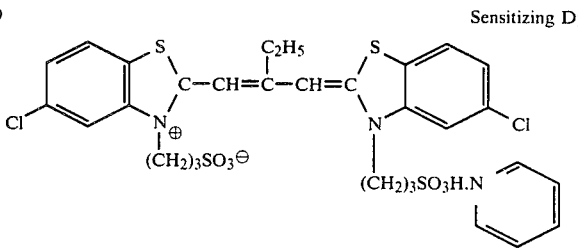
Sensitizing Dye I
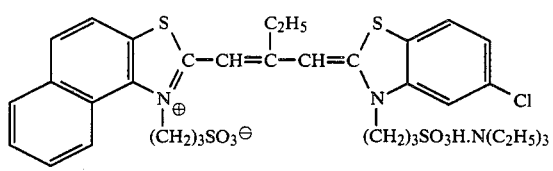
Sensitizing Dye II
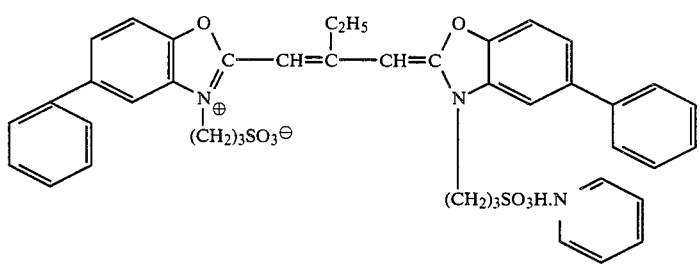
Sensitizing Dye III
Sensitizing Dye IV
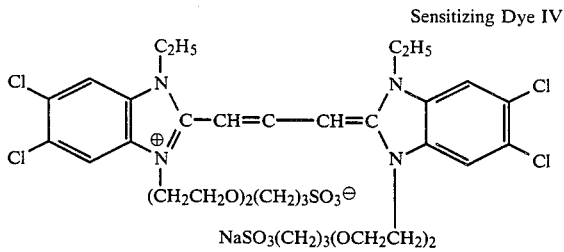
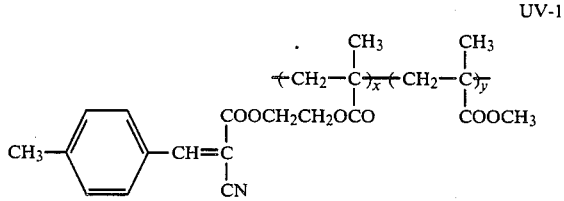
H-1
UV-1
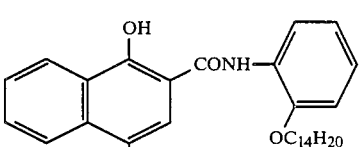
x/y = 7/3 (weight ratio)
EX-10 (Comparison)
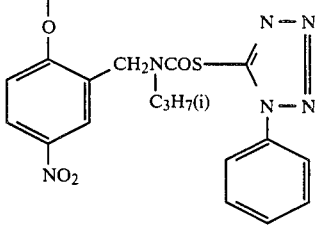

EX-11 (Comparison)

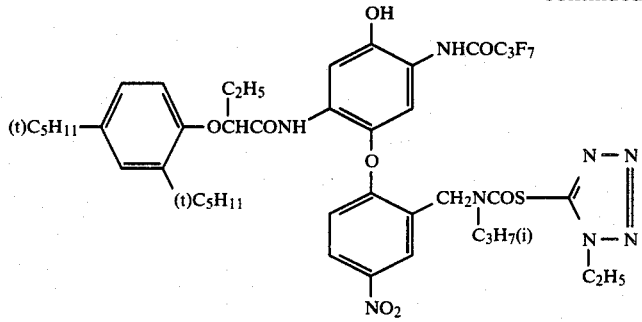

EX-12 (Comparison)

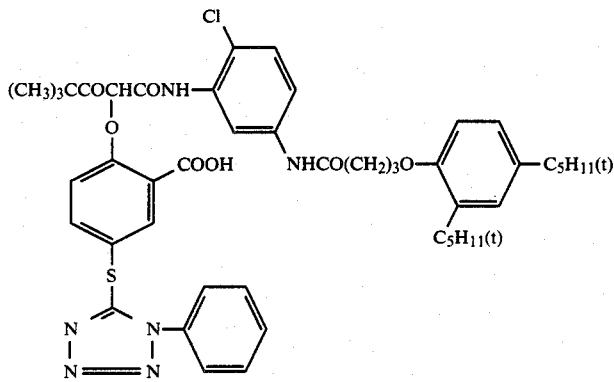

Samples 101 to 109 were subjected to wedge exposure to white light and then processed in the same manner as described in Example 4. The sample thus-processed exhibited almost same sensitivity and gradation. The sharpness of the red-sensitive layers of these samples were evaluated using conventional MTF values The results are shown in Table 5 below.

TABLE 5

| Sample | DIR Coupler used | | MTF Value (20 cycles/mm) |
|---|---|---|---|
| | Coupler** | Amount* | |
| 101 (Invention) | (34) | 1.0 | 0.51 |
| 102 (Invention) | (35) | 0.5 | 0.50 |
| 103 (Invention) | (36) | 1.5 | 0.53 |
| 104 (Invention) | (37) | 0.3 | 0.49 |
| 105 (Invention) | (38) | 0.5 | 0.51 |
| 106 (Invention) | (39) | 1.5 | 0.53 |
| 107 (Comparison) | EX-10 | 0.5 | 0.43 |
| 108 (Comparison) | EX-11 | 1.0 | 0.46 |
| 109 (Comparison) | EX-12 | 1.0 | 0.43 |

*Amount added is indicated using a molar ratio taking the mole of Coupler (34) added in Sample 101 as 1.
**Compound(s) added in place of Coupler (34) to the first red sensitive emulsion layer.

From the results shown in Table 5, it is understood that the MTF values in case of using the coupler according to the present invention are extremely high in comparison with in case of using the comparison DIR couplers.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, the color photographic light-sensitive material containing a coupler which releases a compound after the coupling reaction with the oxidation product of a developing agent, the released compound further releasing a photographically useful group by an oxidation-reduction reaction with the oxidation product of a developing agent, wherein the coupler is represented by the following general formula (I):

$$A-RED-PUG \quad (I)$$

wherein A represents a coupler residue which releases the RED—PUG group upon the coupling reaction with the oxidation product of a developing agent; RED represents a group which releases the PUG group after the oxidation-reduction reaction with the oxidation product of a developing agent after the bonding to A is cleaved selected from the group consisting of a hydroquinone, a catechol, a naphthohydroquinone, an o-amino or p-amino phenol or a bisphenol; and PUG represents a group which exerts a substantial photographic function after the bonding to RED is cleaved.

2. A silver halide color photographic light-sensitive material as claimed in claim 1, wherein A represents a yellow color image forming coupler residue of pivaloyl acetanilide type, benzoyl acetanilide type, malonic diester type, malondiamide type, dibenzoylmethane type, benzothiazolyl acetamide type, malonic ester monoamide type, benzothiazolyl acetate type, benzoxazolyl acetamide type, benzoxazolyl acetate type, benzimidazolyl acetamide type or benzimidazolyl acetate type.

3. A silver halide color photographic light-sensitive material as claimed in claim 1, wherein A represents a magenta color image forming coupler residue of 5-oxo-2-pyrazoline type, pyrazolobenzimidazole type, pyrazoloimidazole type, pyrazolopyrazole type, pyrazolotetrazole type, pyrazolotriazole type or cyanoacetophenone type.

4. A silver halide color photographic light-sensitive material as claimed in claim 1, wherein A represents a cyan color image forming coupler residue of phenol type or α-naphthol type.

5. A silver halide color photographic light-sensitive material as claimed in claim 1, wherein A represents a non-color forming coupler residue of indanone type or acetophenone type.

6. A silver halide color photographic light-sensitive material as claimed in claim 1, wherein PUG represents a group of a development inhibitor, a development accelerator, a fogging agent, a dye, a silver removing accelerator, a silver removing inhibitor, a silver halide solvent or a competing compound.

7. A silver halide color photographic light-sensitive material as claimed in claim 1, wherein the coupler is represented by the following general formula (IIa), (IIb) or (IIc):

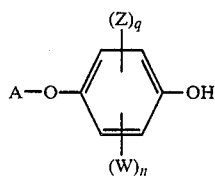

(IIa)

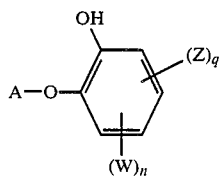

(IIb)

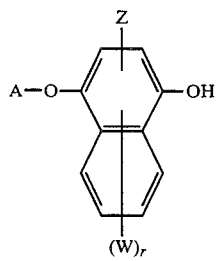

(IIc)

wherein Z represents a development inhibitor group; W represents a substituent selected from a halogen atom, an alkyl group, an alkoxy group, an alkylthio group, an arylthio group, an aryloxy group, a carbamoyl group, an N-alkyl(or dialkyl)carbamoyl group, an alkoxycarbonyl group, an aryloxycarbonyl group, an alkylsulfonyl group, an arylsulfonyl group, a sulfamoyl group, an N-alkyl(or dialkyl)sulfamoyl group, an N-arylcarbamoyl group, an N-arylsulfamoyl group, an alkanoyl group, arylcarbonyl group, a ureido group, an N-alkyl(or dialkyl)ureido group, an N-arylureido group, an alkylamido group, a benzamido group, an imido group, a nitro group, a cyano group, an alkylsulfonamido group, an arylsulfonamido group, a 5-membered or 6-membered heterocyclic group (containing as a hetero atom, a sulfur atom, a nitrogen atom or an oxygen atom), a hydroxy group, a carboxy group, an alkanoyloxy group, a urethane (including an N-alkyl urethane) group, a sulfo group, an amino group which may be substituted with an alkyl group or an aryl group, and an alkoxycarbonylamino group; q represents an integer from 1 to 2; n represents 0 or an integer from 1 to 3; q+n is not more than 4; r represents 0 or an integer from 1 to 5; and A has the same meaning as defined in the general formula (I).

8. A silver halide color photographic light-sensitive material as claimed in claim 1, wherein A represents a coupler residue represented by the following general formula (III) or (IV):

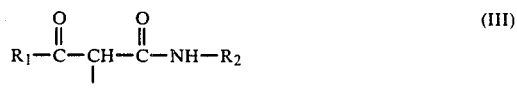

(III)

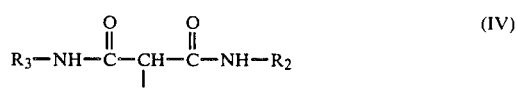

(IV)

wherein $R_1$ represents an aliphatic group, an aromatic group, an alkoxy group or a heterocyclic group; and $R_2$ and $R_3$ each represents an aromatic group or a heterocyclic group.

9. A silver halide color photographic light-sensitive material as claimed in claim 8, wherein the aliphatic group represented by $R_1$ is an alkyl group which may be substituted with a substituent selected from an alkoxy group, an aryloxy group, an amino group, an acylamino group and a halogen atom.

10. A silver halide color photographic light-sensitive material as claimed in claim 8, wherein the aromatic group represented by $R_1$, $R_2$ or $R_3$ is a phenyl group which may be substituted with a substituent selected from an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, an alkyl-substituted succinimido group each containing 32 or less carbon atoms, an aryloxy group, an aryloxycarbonyl group, an arylcarbamoyl group, an arylamido group, an arylsulfamoyl group, an arylsulfonamido group, an arylureido group, an amino group, a hydroxy group, a carboxy group, a sulfo group, a nitro group, a cyano group, a thiocyano group and a halogen atom.

11. A silver halide color photographic light-sensitive material as claimed in claim 8, wherein the aromatic group represented by $R_1$, $R_2$ or $R_3$ is a naphthyl group, a quinolyl group, an isoquinolyl group, a chromanyl group, a coumaranyl group or a tetrahydronaphthyl group.

12. A silver halide color photographic light-sensitive material as claimed in claim 8, wherein the alkoxy group represented by $R_1$ is an alkoxy group in which the alkyl moiety represents a straight chain or branched chain alkyl group having from 1 to 32 carbon atoms, an alkenyl group, a cyclic alkyl group or a cyclic alkenyl group each of which may be substituted with a substituent selected from a halogen atom, an aryl group and an alkoxy group.

13. A silver halide color photographic light-sensitive material as claimed in claim 8, wherein the heterocyclic group represented by $R_1$, $R_2$ or $R_3$ is a group derived from a hetero ring selected from thiophene, furan, pyran, pyrrole, pyrazole, pyridine, pyrazine, pyrimidine, pyridazine, indolizine, imidazole, thiazole, oxazole, triazine, thiadiazole and oxazine.

14. A silver halide color photographic light-sensitive material as claimed in claim 1, wherein A represents a coupler residue represented by the following general formula (V), (VI), (VII) or (VIII):

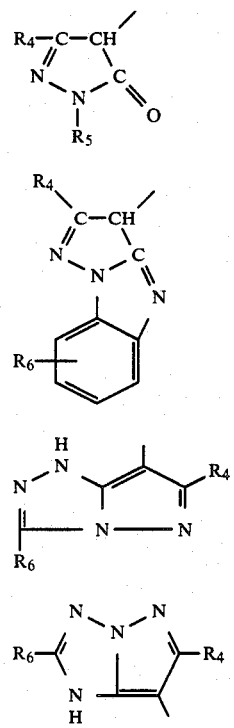

wherein R₅ represents a straight chain or branched chain alkyl group having from 1 to 32 carbon atoms, an alkenyl group, a cyclic alkyl group, an aralkyl group or a cyclic alkenyl group each of which may be substituted with a substituent selected from a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group and a mercapto group; an aryl group which may be substituted with a substituent selected from an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group and a mercapto group; a heterocyclic group which may be substituted with a substituent selected from the substituents as defined for the above-described aryl group; an aliphatic acyl group; an aromatic acyl group; alkylsulfonyl group; an arylsulfonyl group; an alkylcarbamoyl group; an arylcarbamoyl group; an alkylthiocarbamoyl group; or an arylthiocarbamoyl group; R₄ represents a hydrogen atom; a straight chain or branched chain alkyl group having from 1 to 32 carbon atoms, an alkenyl group, a cyclic alkyl group, an aralkyl group, a cyclic alkenyl group an aryl group or a heterocyclic group each of which may be substituted with a substituent selected from the substituents as defined for these groups of R₅ respectively; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a urethane group; a thiourethane group; an arylamino group; an alkylamino group; a cycloamino group; a heterocyclic amino group; an alkylcarbonyl group; an arylcarbonyl group; a sulfonamido group; a carbamoyl group; a sulfamoyl group; a cyano group; a hydroxy group; a mercapto group; a halogen atom; or a sulfo group; and R₆ represents a hydrogen atom; a straight chain or branched chain alkyl group having from 1 to 32 carbon atoms, an alkenyl group, a cyclic alkyl group, an aralkyl group, a cyclic alkenyl group, an aryl group or a heterocyclic group each of which may be substituted with a substituent selected from the substituents as defined for these groups of R₅ respectively; a cyano group; an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

15. A silver halide color photographic light-sensitive material as claimed in claim 14, wherein R₅ represents a phenyl group which is substituted with an alkyl group, an alkoxy group or a halogen atom in at least one of the o-positions.

16. A silver halide color photographic light-sensitive material as claimed in claim 1, wherein A represents a coupler residue by the following general formula (IX), (X), (XI) or (XII)

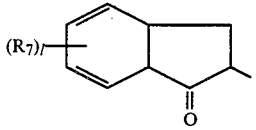 (XII)

wherein $R_7$ represents a hydrogen atom, a halogen atom, an alkoxycarbonylamino group, an aliphatic hydrocarbon residue, an N-arylureido group, an acylamino group, an —O—$R_{12}$ group or an —S—$R_{12}$ group (wherein $R_{12}$ represents an aliphatic hydrocarbon residue); $R_8$ and $R_9$ each represents an aliphatic hydrocarbon residue, an aryl group or a heterocyclic group, one of $R_8$ and $R_9$ may be a hydrogen atom, or $R_8$ and $R_9$ may combine with each other to form a nitrogen-containing heterocyclic nucleus; l represents an integer of 1 to 4; m represents an integer of 1 to 3; and p represents an integer of 1 to 5.

17. A silver halide color photographic light-sensitive material as claimed in claim 16, wherein the aliphatic hydrocarbon group, the aryl group or the heterocyclic group represented by $R_7$, $R_8$ or $R_9$ may be substituted with a substituent selected from a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group and a morpholino group.

18. A silver halide color photographic light-sensitive material as claimed in claim 1, wherein A represents a coupler residue represented by the following general formula (XIII):

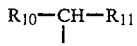 (XIII)

wherein $R_{10}$ represents an arylcarbonyl group, an alkanoyl group having from 2 to 32 carbon atoms, an arylcarbamoyl group, an alkanecarbamoyl group having from 2 to 32 carbon atoms, an alkoxycarbonyl group having from 2 to 32 carbon atoms or an aryloxycarbonyl group each of which may be substituted with a substituent selected from an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group and an aryl group; and $R_{11}$ represents an arylcarbonyl group, an alkanoyl group having from 2 to 32 carbon atoms, an arylcarbamoyl group; an alkanecarbamoyl group having from 2 to 32 carbon atoms, an alkoxycarbonyl group having from 2 to 32 carbon atoms, an aryloxycarbonyl group, an alkanesulfonyl group having from 1 to 32 carbon atoms, an arylsulfonyl group, an aryl group or a 5-membered or 6-membered heterocyclic group each of which may be substituted with a substituent selected from the substituents as defined for $R_{10}$.

19. A silver halide color photographic light-sensitive material as claimed in claim 7, wherein the development inhibitor group represented by Z is represented by the following general formula (XIV) to (XXII):

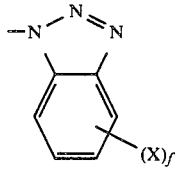 (XIV)

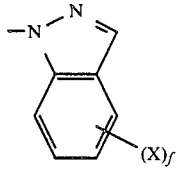 (XV)

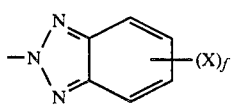 (XVI)

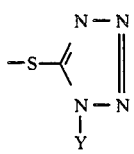 (XVII)

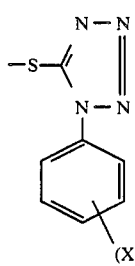 (XVIII)

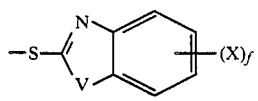 (XIX)

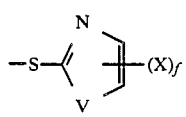 (XX)

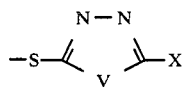 (XXI)

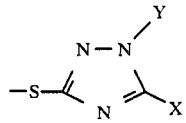 (XXII)

wherein X represents a substituent selected from a hydrogen atom, a halogen atom, an alkyl group, an alkanamido group, an alkoxy group, a sulfonamido group, an aryl group, an alkylthio group, an amino group, an N-(mono- or di-alkyl)amino group, an arylthio group, an alkoxycarbonyl group, an acyloxy group, a carbamoyl group, an N-(mono- or dialkyl)carbamoyl group, a nitro group, a cyano group, an alkanesulfonyl group, an aryloxy group, a ureido group, a sulfamoyl group, a hydroxy group, an anilino group, a heterocyclic group, a sulfenamido group and a carboxy group; Y represents a substituent selected from a hydrogen atom, an alkyl group, a phenyl group and a heterocyclic group; V represents —O—, —S— or

wherein Y has the same meaning as defined above; and f represents an integer of 1 to 2, when f represents 2, X's may be the same or different.

20. A silver halide color photographic light-sensitive material as claimed in claim 1, wherein the compound is present in a silver halide emulsion layer.

21. A silver halide color photographic light-sensitive material as claimed in claim 20, wherein the compound is present in an amount ranging from $1 \times 10^{-6}$ mol to 1 mol per mol of silver in the silver halide emulsion layer.

22. A silver halide color photographic light-sensitive material as claimed in claim 1, wherein the photographic light-sensitive material contains at least one red-sensitive silver halide emulsion layer containing at least one cyan color forming coupler, at least one green-sensitive silver halide emulsion layer containing at least one magenta color forming coupler and at least one blue-sensitive silver halide emulsion layer containing at least one yellow color forming coupler and at least one of these cyan, magenta and yellow color forming couplers is a coupler represented by the general formula (I).

* * * * *